(12) United States Patent
Barbeyron et al.

(10) Patent No.: US 6,333,185 B1
(45) Date of Patent: Dec. 25, 2001

(54) GLYCOSYL HYDROLASE GENES AND THEIR USE FOR PRODUCING ENZYMES FOR THE BIODEGRADATION OF CARRAGEENANS

(75) Inventors: Tristan Barbeyron, Cleder; Philippe Potin, Roscoff; Christophe Richard, Plougourvest; Bernard Henrissat, Uriage; Jean-Claude Yvin, Saint Malo; Bernard Kloareg, Saint Pol de Leon, all of (FR)

(73) Assignee: Laboratories Goemar S.A., Saint Malo (FR)

( * ) Notice: Subject to any disclaimer, the term of this patent is extended or adjusted under 35 U.S.C. 154(b) by 0 days.

(21) Appl. No.: 09/269,731

(22) PCT Filed: Oct. 6, 1997

(86) PCT No.: PCT/FR97/01768

§ 371 Date: Apr. 5, 1999

§ 102(e) Date: Apr. 5, 1999

(87) PCT Pub. No.: WO98/15617

PCT Pub. Date: Apr. 16, 1998

(30) Foreign Application Priority Data

Oct. 7, 1996 (FR) .................................................. 96 12204

(51) Int. Cl.[7] ....................................................... C12N 9/24
(52) U.S. Cl. .................... 435/200; 435/252.3; 435/320.1; 536/23.2
(58) Field of Search ................................ 435/206, 320.1, 435/252.3; 536/23.2

(56) References Cited

PUBLICATIONS

Barbeyron, T., et al. (1994) Gene 139, 105–109.*

* cited by examiner

*Primary Examiner*—Charles L. Patterson, Jr.
(74) *Attorney, Agent, or Firm*—Dennison, Scheiner, Schultz & Wakeman

(57) ABSTRACT

The present invention relates to genes which code for glycosyl hydrolases having an HCA score with the iota-carrageenase of *Alteromonas fortis* which is greater than or equal to 65% over the domain extending between amino acids 164 and 311 of the protein sequence SEQ ID No. 2 of said iota-carrageenase, and to genes which code for glycosyl hydrolases having an HCA score with the kappa-carrageenase of *Alteromonas carrageenovora* which is greater than or equal to 75% over the domain extending between amino acids 117 and 262 of the protein sequence SEQ ID No. 6 of said kappa-carrageenase.

7 Claims, 7 Drawing Sheets

```
                                       ↓      ↓ ↓
 27        AVSPKTYKDADFYVAPIQQDVNY___DLVDDFGANGNDTSD  64
           |    |   |  |      |  |    || |    ||  ||
 28        DTSEISEVPTELRAAASSFYTPPGQNVRANKKNLVTDYGVNHNDQND  74
           ↓                                ↓
 65  DSNALQRAINAISRKPNGGTLLIPNGIYHFLGIQMKSNVHIRVESDVIIK  114
     ||    |   ||    |    ||  |  |     | | ||||   |     |
 75  DSSKLNLAIKDLS__DTGGILTLPKGKYYLTKIRMRSNVHLEIEKGTVIY  122
                                             ↓
115  PTWN GDGKNHRLFEVG__VNNIVRNFSFQGLGNGFLVDFKDSRDKNLAV  161
     ||    ||||  |        | | || |  | |       ||    |
123  PTKGLTPAKNHRIFDFASKTEEKIENASIVGKGGKFIVDLRGNSSKNQIV  172
           ↓                                   ↓
162  FKLGDVRNYKISNFTIDDNKTIFASILVDVTERNGRLHWSRNGIIERIKQ  211
     |  |   |||||||| |  ||||||||| |    |   |  ||||  ||
173  ADVGNVINFKISNFTIKDEKTIFASILVSFTDKAGN_AWPHKGIIENIDQ  221
                  ↓                               ↓↓
212  NNALFGYGLIQTYGADNILFRNLHSEGGIALRMETDNLLMKNYKQGGIRN  261
     ||   ||||||| |  ||||||  || || || ||||| || |  |||
222  ANAHTGYGLIQAYAADNILFNNLSCTGGVTLRLETDNLAMKIAKKGGVRD  271
                                                        ↓
262  IFADNIRCSKGLAAVMFGPHFMKNGDVQVINVSSVSCGSAVRSDSGFVEL  311
     |||   |   ||  |||   |||| ||  |    |     |||    ||
272  IFATKIKNINGLTPVMFSPHFMENGKVTIDDVTAIGCAYAVRVEHGFIEI  321
                                    ↓
312  FSPTDEVHTRQSWKQAVESKLGRGCAQTPYARGNGGTRWAARVT___QKD  358
     |           |  |     |   | || |    |   | ||||
322  FDKGNRASA_DAFKNYIEGILGAGSVEVVYKRNNGRT_WAARIANDFNEA  369

359  ACLDKAKLEYGIEPGSFGTVKVFDVTARF_GYNADLKQDQLDYFSTSNPM  407
     |     ||  || ||   |   |   |   |  |   ||   |  |  |
370  AYNHSNPAVSGIKPGKFATSKVTNVKATYKGIGAKLKQAFLSYLPCSER_  418
                                     ↓
408  CKRVCLPTKEQWSKQGQIYIGPSLAAVID_TTPETSKYDYLVKTFNVKRI  457
     | ||          |   |||   ||  |        |  |
419  SK_VCRPGPDGFE___YNGPSLGVTIDNTKRDNSLGNYNVNVSTSSVQ  462

457  NFPVNSHKTIDINTESSRVCNYY_GMSECSSSRWER       491
     |   |         | |   ||    |   | |  |
463  GFPNNYVLNVKYNT__PKVCNQNLG_SITSCN           491
```

FIG.1

FIG.2 (CONTINUATION)

```
  1 MKKPNFYGKMGRTALSSLFYLFFLGLVYGQQPTKTSNPNDQWTIKWSASDEFN_KNDPDW     59
                         ||    ||                    ||||||||  ||||||
  1 MKPISIVAFPIPAISMLLLSAVSQAASM_QPPIAK_PGETWILQAKRSDEFNVK_DAT_     55

60 AKWIK_TGNLPNTSAWKWN_NQKNVKISNGIAELTM_RHNANNTPPDGT            YF   108
     |||| |  |  |    ||   |||  |||  |||                         ||
 56 KWNFQTENYGVWS_WK_NENAT_V__SNGKLKLTTKRESHQRTFWDGCNQQQVANYPLY      109

109 _TSGIFKSYQKFTYGYFEAKIQGADIGEGVCPSFWLYSDFDYSVAN_GETVYSEIDVVEL    166
     |||   ||| || |   | |    ||    |    |||  |||  |  ||||||||||
110  YTSGVAKSRATGNYGYYEARIKGASTFPGVSPAFWMYSTIDRSLTKEGDVQYSEIDVVEL   169

167 QQFDWY_EGHQDDIYDMDINLHAVVKENGQGVWKRPKMYPQEQLNKWRAM_DPSKDFHIY    224
     | |     |  ||  |      |  |    ||| |  |  | |||| |  | | |||
170 TQKSAVRES_DH__DLH_NI__VVK_NGKPTWMRPGSFPQTNHNGYHLPFDPRNDFHTY     221

225 GCEVNQNEIIWYVDGVE_VARKPNKYWHRPMNVTLSLGLRKPFVKFFDNKNNAINPETDA   283
     |  | |   ||| ||    | ||  ||| ||| |||||   |   |
222 GVNVTKDKITWYVDG_EIVGEKDNLYWHRQMNLTLSQGLRAPHTQW_KCNQFYPSAN_     276

See_FIG.3
(CONTINUATION) 284 K_AREKLSDIPTSMYVDYVRVWEKSAGNTTNPPTSEVGTLKTKGSKLVIDHWDASTGTIS  342
                    | |                                 |  |
              277 KSA_EGF____PTSMEVDYVRTWVKVGNNNSAPGEGQSCPNTFVAVNSVQLSAAKQTLRKG  332
```

FIG.3

```
284 K_AREKLSDIPTSMYDYVRVWEKSAGNTTNPPTSEVGTLKTKGSKLVIDHWDASTGTIS       342
       | |||  |||| |||||   |  |    |
277 __KSA_EGF___PTSMEVDYVRTWVKVGNNNSAPGEGQSCPNTFVAVNSVQLSAAKQTLRKG    332
See FIG.3

343 AVSNNTKTGQYAGSVNNASIAQIVTLKANTSYKVSAFGKASSPGTSAYLGISKASNNELI      402
      |  | |    | |||    ||   || |||||
333 QSTTLESTVLPNCATNKKVIYSSSNKNVATVNSAGVV_KAKNKGTATITVKTKNKGKIDKL     392

403 SNFEFKTTSYSKGEIEIRTGNVQESYRIWYWSSGQAYCDDFNLVEINSGASQLNENETET     462

393 TIAVN                                                             397

463 ALEKGIHIYPNPYKNGPLTIDFGKPFSGEVQITGLNGRTFLRRNVVDQTSVQLLESKSKF      522

523 KSGLYIVKISGPDGEVSKKILVE                                           545
```

FIG.3 (CONTINUATION)

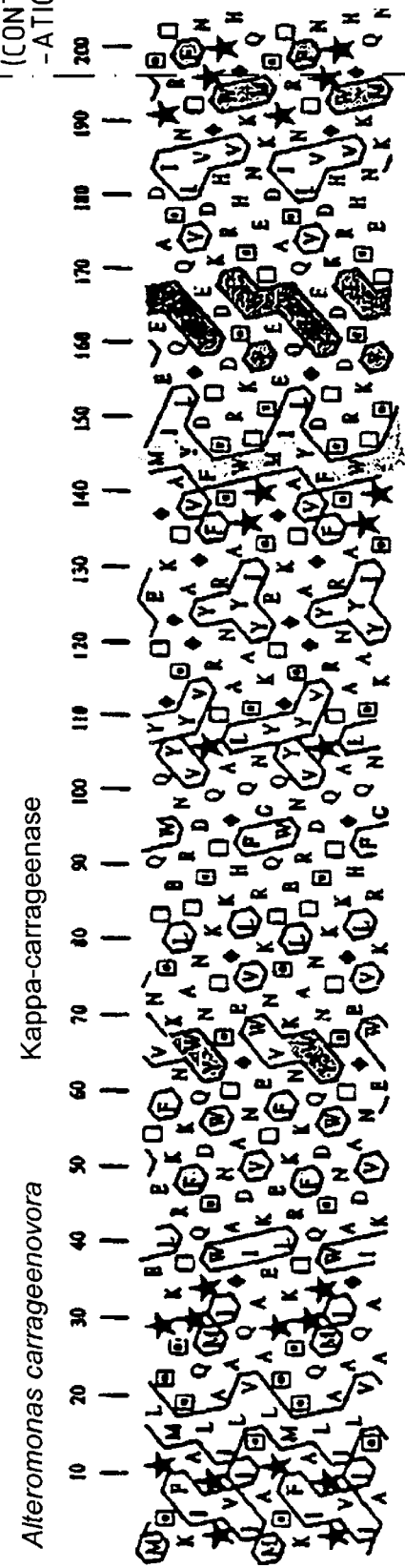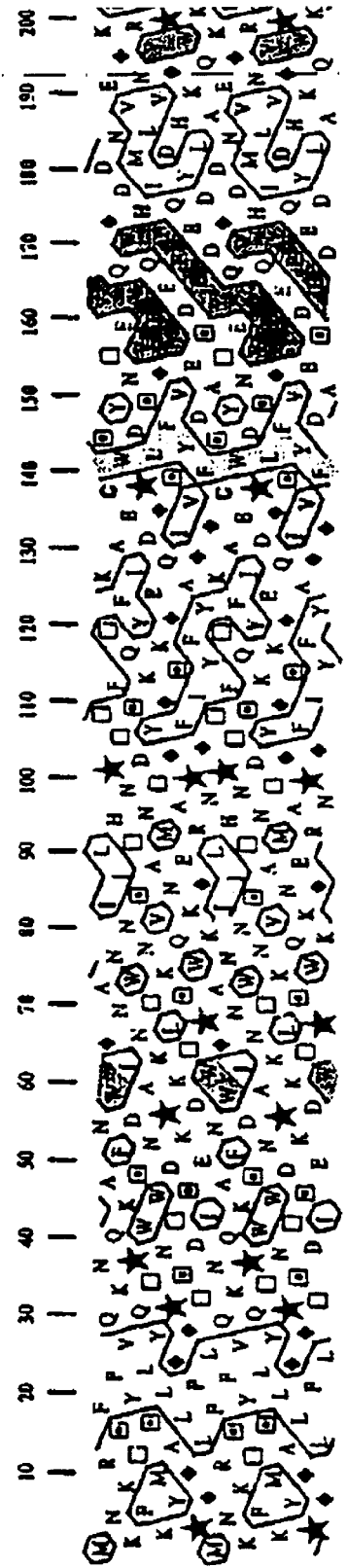
FIG. 4

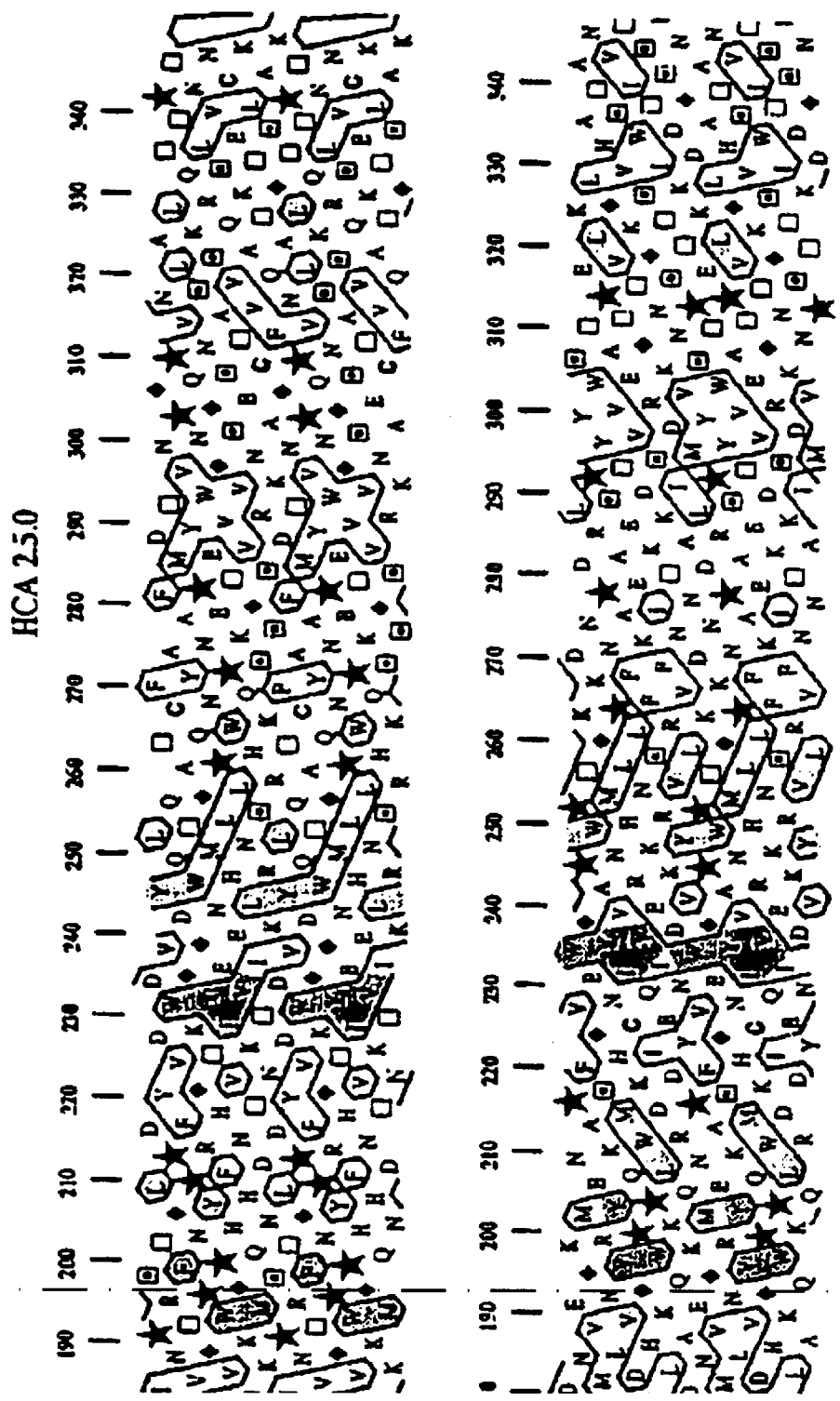
FIG.4 (CONTINUATION)

GLYCOSYL HYDROLASE GENES AND THEIR USE FOR PRODUCING ENZYMES FOR THE BIODEGRADATION OF CARRAGEENANS

BACKGROUND OF THE INVENTION

The present invention relates to glycosyl hydrolase genes for the biotechnological production of oligosaccharides, especially sulfated oligocarrageenans and more particularly oligo-iota-carrageenans and oligo-kappa-carrageenans, by the biodegradation of carrageenans.

The sulfated galactans of Rhodophyceae, such as agars and carrageenans, represent the major polysaccharides of Rhodophyceae and are very widely used as gelling agents or thickeners in various branches of activity, especially agri-foodstuffs. About 6000 tonnes of agars and 22,000 tonnes of carrageenans are extracted annually from red seaweeds for this purpose. Agars are commercially produced by red seaweeds of the genera Gelidium and Gracilaria. Carrageenans, on the other hand, are widely extracted from the genera Chondrus, Gigartina and Eucheuma.

Carrageenans consist of repeat D-galactose units alternately bonded by $\beta 1 \rightarrow 4$ and $\alpha 1 \rightarrow 3$ linkages. Depending on the number and position of sulfate ester groups on the repeat disaccharide of the molecule, carrageenans are thus divided into several different types, namely: kappa-carrageenans, which possess one sulfate ester group, iota-carrageenans, which possess two sulfate ester groups, and lambda-carrageenans, which possess three sulfate ester groups.

The physicochemical properties and the uses of these polysaccharides as gelling agents are based on their capacity to undergo ball-helix conformational transitions as a function of the thermal and ionic environment [Kloareg et al., Oceanography and Marine Biology—An annual review 26: 259–315 (1988)].

Furthermore, carrageenans are structural analogs of the sulfated polysaccharides of the animal extracellular matrix (heparin, chondroitin, keratan, dermatan) and they exhibit biological activities which are related to certain functions of these glycosaminoglycans.

In particular, carrageenans are known:
 (i)—for their action on the immune system, causing the secretion of interleukin or prostaglandins,
 (ii)—for their antiviral action on the AIDS virus HIV1, the herpes virus HSV1 and the hepatitis A virus,
 (iii)—as antagonists of the fixation of the growth factors of human cells,
 (iv)—and also for their action on the proliferation of keratinocytes and their action on the contractility of fibroblasts.

Furthermore, oligocarrageenans act on the adherence, the division and the protein synthesis of human cell cultures, doubtless as structural analogs of the glycosylated part of the proteins of the extracellular matrix. In plants, oligocarrageenans very significantly elicit enzymatic activities which are markers of growth (amylase) or of the phenolic defense metabolism (laminarinase, phenyl-alanineammonium lyase).

Carrageenans are extracted from red seaweeds by conventional processes such as hot aqueous extraction, and oligocarrageenans are obtained from carrageenans by chemical hydrolysis or, preferably, by enzymatic hydrolysis.

The production of oligocarrageenans by enzymatic hydrolysis generally comprises the following steps:
 1) production of a glycosyl hydrolase by the culture of a marine bacterium;
 2) enzymatic hydrolysis of the carrageenan with the glycosyl hydrolase thus obtained; and
 3) fractionation and purification of the oligocarrageenans obtained.

Microorganisms which produce enzymes capable of hydrolyzing iota- and kappa-carrageenans were isolated by Bellion et al. in 1982 [Can. J. Microbiol. 28: 874–80 (1982)]. Some are specific for κ- or ι-carrageenan and others are capable of hydrolyzing both substrates. Another group of bacteria capable of degrading carrageenans was characterized by Sarwar et al. in 1983 [J. Gen. Appl. Microbiol. 29: 145–55 (1983)]. These yellow-orange bacteria are assigned to the Cytophaga group of bacteria and some of these bacteria have the property of hydrolyzing both agar and carrageenans.

Purification and characterisation of several ι-carrageenases and κ-carrageenases, such as the ι-carrageenase and κ-carrageenase of *Cytophaga drobachiensis*, the ι-carrageenase of *Alteromonas fortis* and the κ-carrageenase of *Alteromonas carrageenovora*, were described in the thesis of P. Potin ["Recherche, production, purification et caractérisation de galactane-hydrolases pour la préparation des parois d'algues rouges", (February 1992)]. A detailed study of the κ-carrageenase of *Alteromonas carrageenovora* was described by Potin et al. [Eur. J. Biochem. 228, 971–975 (1995)].

The availability of specific enzymes and tools for obtaining oligocarrageenans by genetic engineering could markedly improve their production.

SUMMARY OF THE INVENTION

The Applicant has now found novel glycosyl hydrolase genes which make it possible specifically to obtain either oligo-iota-carrageenans or oligo-kappa-carrageenans.

Thus the present invention relates to novel genes which code for glycosyl hydrolases having an HCA score with the iota-carrageenase of *Alteromonas fortis* which is greater than or equal to 65%, preferably greater than or equal to 70% and advantageously greater than or equal to 75% over the domain extending between amino acids 164 and 311 of the sequence [SEQ ID No. 2] of the iota-carrageenase of *Alteromonas fortis*.

The present invention relates more particularly to the nucleic acid sequence [SEQ ID No. 1] which codes for an iota-carrageenase as defined above, the amino acid sequence of which is the sequence [SEQ ID No. 2].

The present invention further relates to the genes which code for glycosyl hydrolases having an HCA score with the kappa-carrageenase of *Alteromonas carrageenovora* which is greater than or equal to 75%, preferably greater than 80% and advantageously greater than 85% over the domain extending between amino acids 117 and 262 of the sequence [SEQ ID No. 6] of the kappa-carrageenase of *Alteromonas carrageenovora*.

In particular, the invention relates to the nucleic acid sequence [SEQ ID No. 7] which codes for a kappa-carrageenase having a score as defined above, the amino acid sequence of which is the sequence [SEQ ID No. 8].

The glycosyl hydrolase genes of the invention are obtained by a process which consists in selecting proteins having an HCA score with the iota-carrageenase of *Alteromonas fortis* which is greater than or equal to 65%, preferably greater than or equal to 70% and advantageously greater than or equal to 75% over the domain extending between amino acids 164 and 311 of the sequence [SEQ ID No. 2] of the iota-canageenase of *Alteromonas fortis*, and in sequencing the resulting genes by the conventional techniques well known to those skilled in the art.

The glycosyl hydrolase genes of the invention can also be obtained by a process which consists in selecting proteins having an HCA score with the kappa-carrageenase of *Alteromonas carrageenovora* which is greater than or equal to 75%, preferably greater than 80% and advantageously greater than 85% over the domain extending between amino acids 117 and 262 of the sequence [SEQ ID No. 6] of the kappa-carrageenase of *Alteromonas carrageenovora*, and in sequencing the resulting genes by the conventional techniques well known to those skilled in the art.

Finally, the present invention relates to the use of the above glycosyl hydrolase genes for obtaining, by genetic engineering, glycosyl hydrolases which are useful for the biotechnological production of oligocarrageenans.

The glycosyl hydrolases according to the invention are therefore characterized by the HCA score which they possess with a particular domain of the amino acid sequence of the iota-carrageenase of *Alteromonas fortis* or the kappa-carrageenase of *Alteromonas carrageenovora*.

The HCA or "Hydrophobic Cluster Analysis" method is a method of analyzing the sequences of proteins represented as a two-dimensional structure, which has been described by Gaboriaud et al. [FEBS Letters 224, 149–155 (1987)].

It is known that the three-dimensional structure of a protein governs its biological properties, the production of an active protein demanding correct folding.

It is also known that the primary structure of proteins varies much more substantially than the higher-order structures and that proteins can be grouped into families which show similar secondary and tertiary structures but sometimes have such divergent primary sequences that the mutual relationship between such proteins is not obvious. The code which relates primary structure and secondary structure therefore appears to be highly degenerate since very different primary structures can ultimately lead to similar secondary and tertiary structures [Structure 3, 853–859 (1995) and Proc. Natl. Acad. Sci. USA 92 (1995)].

The use of the HCA method has shown that the distribution, size and shape of these hydrophobic clusters along the amino acid sequences are representative of the 3D folding of the proteins studied.

Also, Woodcock et al. [Protein Eng. 5, 629–635 (1992)] have shown that the hydrophobic clusters defined by the α-helical 2D diagram are statistically centered on the regular secondary structures (α-helices, β-strands), that the 2D diagram based on the α-helix carries the greatest amount of structural information and that the correspondence between hydrophobic clusters and elements of secondary structure is of the same quality for any type of folding (all α, all β, α/β and α+β), thus demonstrating that the HCA method can be used irrespective of the type of protein.

L. Lemesle-Varloot et al. [Biochimie 72, 555–574 (1990)] have shown that when two proteins have a similar distribution of hydrophobic clusters over a domain of at least 50 residues, their three-dimensional structures in this domain are considered to be superimposable and their functions to be analogous.

Thus, for example, Barbeyron et al. [Gene 139, 105–109 (1994)] used this HCA method for the comparison of the similarities in the shape, distribution and size of several hydrophobic clusters of the κ-carrageenase of *Alteromonas carrageenovora* with respect to enzymes from family 16 of glycosyl hydrolases.

The two-dimensional representation used in the HCA method is an α-helix in which the amino acids are arranged by computer processing to give 3.6 residues per turn. To obtain an easily readable plane image, the helix is cut in the longitudinal direction. Finally, to obtain the whole of the hydrophobic clusters situated at the edges of the image, the diagram is duplicated. The method uses a code which recognizes only two states: the hydrophobic state and the hydrophilic state.

The amino acids recognized as being hydrophobic are identified and grouped into characteristic geometric figures. Using these two states makes it possible to become independent of the tolerance shown by the two- and three-dimensional structures towards the variability of the primary sequences. Furthermore, this representation affords rapid observation of interactions over a short or medium distance since the first amino acid and the second, adjacent amino acid of a given residue are located on a segment of 17 amino acids. Finally, in contrast to the analytical methods based on the primary or secondary structures of proteins, no "window" of predefined length is used.

The fundamental characteristic of the α-helix representation is that, for a given globular protein or only a domain of this protein, the distribution of the hydrophobic residues on the diagram is not random. The hydrophobic residues (VILFWMY) form clusters of varying geometry and size. On the diagram, the hydrophilic and hydrophobic faces of the amphiphilic helices are very recognizable. Thus a horizontal diamond cluster corresponds to the hydrophobic face of an α-helix, the internal helices appear as large horizontal hydrophobic clusters and the β-strands appear as rather short, vertical hydrophobic clusters. The method makes it possible to identify the hydrophobic residues forming the core of the globular proteins and to locate the elements of secondary structure, namely the α-helices and the β-strands, independently of any knowledge of the secondary structure of the protein studied.

The HCA score between two proteins is calculated as follows:

For each cluster:

$$\text{HCA score} = 2CR/(RC_1 + RC_2) \times 100\%$$

where $RC_1$ and $RC_2$ are the number of hydrophobic residues in the cluster of protein 1 (cluster 1) and the cluster of protein 2 (cluster 2), respectively.

CR is the number of hydrophobic residues in the cluster 1 which correspond to the hydrophobic residues in the cluster 2.

The mean value obtained for all the clusters along the protein sequences compared gives the final HCA score.

On the HCA profiles, the amino acids are represented by their standard code of a single letter, with the exception of proline (P), glycine (G), serine (S) and threonine (T).

In fact, because of their particular properties, these residues are represented by the special symbols indicated below so as to facilitate their visual identification on the HCA diagrams (cf. list of abbreviations).

Proline introduces high constraints into the polypeptide chain and is considered systematically as an interruption in the clusters. In fact, proline residues stop or deform the helices and the lamellae. Glycine possesses a very substantial conformational flexibility because of the absence of a side chain in this amino acid. Serine and threonine are normally hydrophilic, but they can also be found in hydrophobic environments, such as α-helices, in which their hydroxyl group loses their hydrophilic character because of the hydrogen bond formed with the carbonyl group of the main chain. Within the hydrophobic β-lamellae, threonine is sometimes capable of replacing hydrophobic residues by virtue of the methyl group on its side chain.

Amino acids can be divided into four groups according to their hydrophobicity:

(i)—strongly hydrophobic residues: V, I, L and F;
(ii)—moderately hydrophobic residues: W, M and Y
   →W appears at surface sites more frequently than F,
   →M is encountered at various sites, internal or otherwise,
   →Y can adapt to internal hydrophobic environments and is frequently found in loops;
(iii)—weakly hydrophobic residues: A and C are virtually insensitive to the hydrophobic character of their environment; and
(iv)—hydrophilic residues: D, E, N, Q, H, K and R.

Using this HCA method, the Applicant has found that proteins having an HCA score with the iota-carrageenase of *Alteromonas fortis* which is greater than or equal to 65% over the domain extending between amino acids 164 and 311 of said iota-carrageenase are enzymes of the glycosyl hydrolase type and more particularly iota-carrageenases appropriate for the production of oligo-iota-carrageenans from carrageenans.

The proteins having an HCA score which is greater than or equal to 70%, preferably greater than or equal to 75%, with the above domain 164–311 are particularly preferred for the purposes of the invention.

One particular example of glycosyl hydrolase obtained with a gene according to the invention is the protein having the amino acid sequence [SEQ ID No. 2], extracted from *Alteromonas fortis*.

Another particular example of glycosyl hydrolase obtained with a gene according to the invention is the protein having the amino acid sequence [SEQ ID No. 4], extracted from *Cytophaga drobachiensis*.

Likewise, the Applicant has found that proteins having an HCA score with the kappa-carrageenase of *Alteromonas carrageenovora* which is greater than or equal to 75% over the domain extending between amino acids 117 and 262 of said kappa-carrageenase are enzymes of the glycosyl hydrolase type and more particularly kappa-carrageenases appropriate for the production of oligo-kappa-carrageenans from carrageenans.

The proteins having an HCA score which is greater than or equal to 80%, preferably greater than or equal to 85%, with the above domain 117–262 are particularly preferred for the purposes of the invention.

The above proteins are advantageously extracted from marine bacteria.

One particular example of glycosyl hydrolase obtained with a gene according to the invention is the protein having the amino acid sequence [SEQ ID No. 6], extracted from *Alteromonas carrageenovora*.

Another particular example of glycosyl hydrolase obtained with a gene according to the invention is the protein having the amino acid sequence [SEQ ID No. 8], extracted from *Cytophaga drobachiensis*.

As indicated previously, the genes according to the invention, coding for glycosyl hydrolases, can be obtained by sequencing the genome of bacteria which product glycosyl hydrolases, as defined above, by the conventional methods well known to those skilled in the art.

The invention further relates to the expression vectors which carry the nucleic acid sequences according to the invention, with the means for their expression.

These expression vectors can be used to transform prokaryotic microorganisms, particularly *Escherichia coli*, or eukaryotic cells such as yeasts or fungi.

The invention will now be described in greater detail by means of the illustrative and non-limiting Examples below.

The methods used in these Examples are methods well known to those skilled in the art, which are described in detail in the work by Sambrook, Fristsch and Maniatis entitled "Molecular cloning: a laboratory manual", published in 1989 by Cold Spring Harbor Press, New York (2nd edition).

BRIEF DESCRIPTION OF THE DRAWINGS

The following description will be understood more clearly with the aid of FIGS. 1 to 4, which respectively show the following:

FIG. 1: The maximum similarity alignment, according to the method of Needleman and Wunsch [J. Mol. Biol. 48, 443–453 (1970)] of the amino acid sequence of the iota-carrageenase of *Alteromonas fortis* (SEQ ID No: 2) (top part) and the iota-carrageenase of *C. drobachiensis* SEQ ID No: 4 (bottom part).

FIG. 4: The HCA profiles of the amino acid sequences of the kappa-carrageenases of *Cytophaga drobachiensis* and *Alteromonas fortis*.

Figure 2:
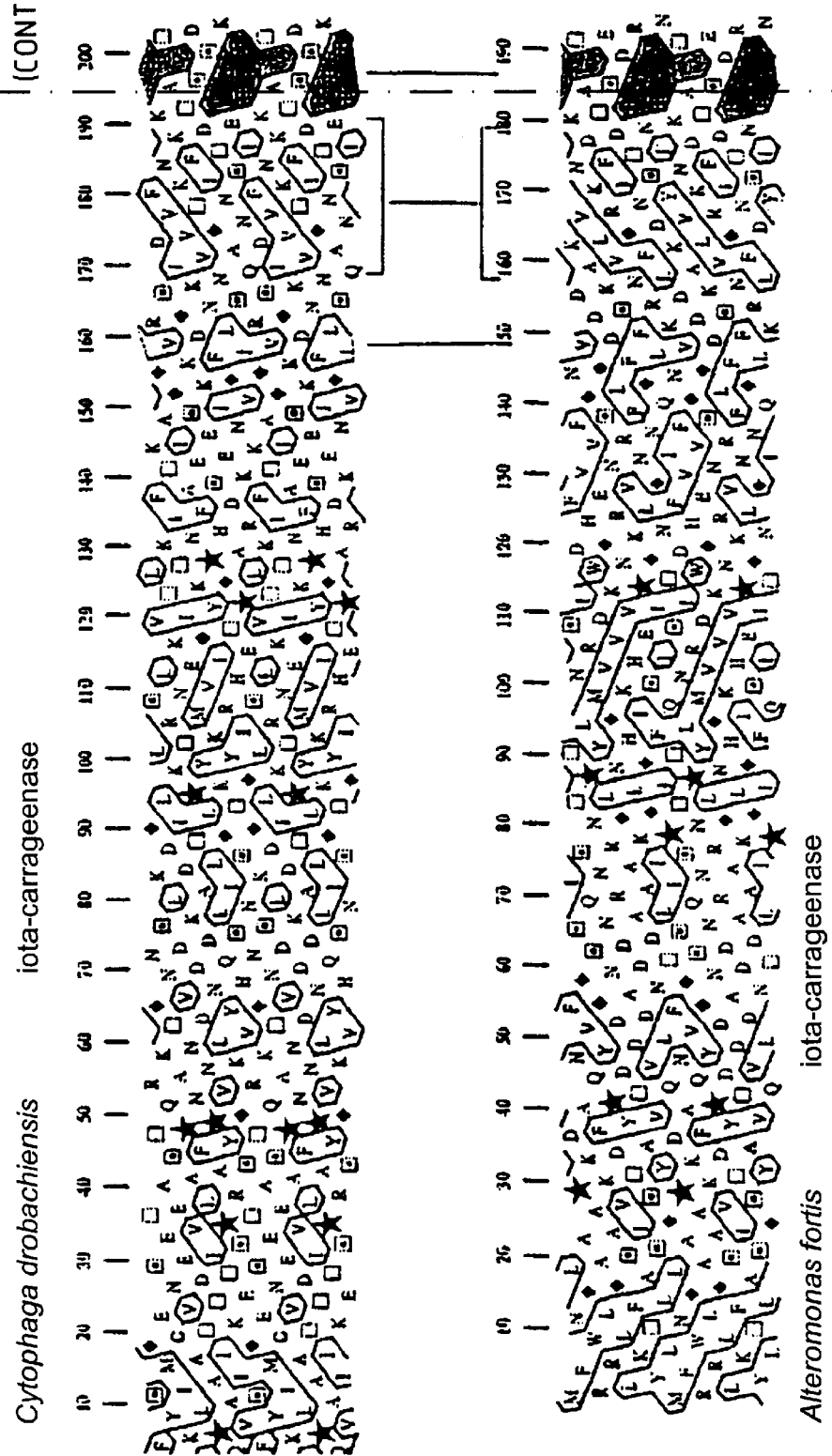
FIG. 2: The HCA profiles of the amino acid sequences of the iota-carrageenases of *Cytophaga drobachiensis* and *Alteromonas fortis*.

The abbreviations or special symbols used for the amino acids in the Examples below are as follows:

Glycine: ◇
Proline: *
Threonine: □
Sérine:▣
Alanine: A
Valine: V
Leucine: L
Isoleucine: I
Methionine: M
Phenylalanine: F
Tryptophan: W
Cysteine: C
Asparagine: N
Glutarnine: Q
Tyrosine: Y
Aspartate: D
Glutamate: E
Lysine: K
Arginine: R
Histidine: H

EXAMPLE 1

The Iota-carrageenases of *Cytophaga drobachiensis* and *Alteromonas fortis*

SECTION 1: Cloning of the genes of the iota-carrageenases of *Cytophaga drobachiensis* and *Alteromonas fortis*

*Cytophaga drobachiensis* was isolated by the Applicant from the red seaweed *Delesseria sanguinea* [Eur. J. Biochem. 201 : 241–247 (1991)]. *Alteromonas fortis* (ATCC 43554) was obtained from the American Type Culture Collection. The strains were cultivated on a Zobell medium at 25° C.

Genome libraries of the DNAs of *C. drobachiensis* and *A. fortis* were constructed.

The strain used to construct these libraries, namely *Escherichia coli* DH5α (Rec A, endA1, gyrA96, thi1, hsdR17 [rk– mk+], supE44, relA1, lacZΔM15), was cultivated on Luria-Bertani medium (LB medium) at 37° C. or on a so-called Zd medium (bactotryptone 5 g/l, yeast extract 1 g/l, NaCl 10 g/l; pH=7.2) at 22° C., to which 2% of κ-carrageenan were added.

Ampicillin (50 µg/ml) or tetracycline (15 µg/ml) was added to the agar or non-agar culture media from stock solutions prepared in 50% ethanol (to avoid solidification at the storage temperature, –20° C.), except in the case of the non-recombinant strain DH5α.

The expression vector used is plasmid pAT153 described in Nature 283:216 (1980). This plasmid contains two antibiotic resistance genes: a tetracycline resistance gene and a gene which codes for a β-lactamase, an enzyme of the cytoplasmic membrane which degrades ampicillin.

The total DNA of *C. drobachiensis* and the total DNA of *A. fortis* were prepared by the method described by Barbeyron et al. [J. Bacteriol. 160, 586–590 (1984)].

The genomic DNAs of *C. drobachiensis* and *A. fortis* were cleaved with the restriction endonucleases NdeII and Sau3AI respectively. In fact, in the case of *C. drobachiensis*, the restriction endonuclease NdeII was used preferentially because the DNA of this bacterium is methylated on the C residue of the GATC sequence.

The purified DNA fragments of 5000 to 10,000 bp were cloned at the BamHI site of plasmid pAT153, which cleaves the tetracycline resistance gene.

6000 clones were obtained in each of the genome libraries.

The five positive *C. drobachiensis* clones and the two positive *A. fortis* clones, which hollowed out a hole in the ι-carrageenan after one week of culture at 22° C., are referred to respectively as pIC1 to pIC5 and pIP1 to pIP2.

1. Cloning from *C. drobachiensis*

The cloning of this gene is described in detail by T. Barbeyron in the doctoral thesis examined on Oct. 28, 1993 at the Université Pierre et Marie Curie, Roscoff.

The plasmid DNA was isolated from the above five clones by the alkaline lysis method [Nucleic Acid Res. 7: 1513 (1979)].

The sizes and mapping of the inserts showing an ι-carrageenase activity were determined by agarose gel electrophoresis after single and double digestion of their plasmids with various restriction enzymes.

The DNA fragments were extracted from the agarose by the glass wool method.

All the plasmids obtained contain an identical PvuII fragment of 3.3 kb.

This fragment was subcloned in phagemid pbluescript KSII (Stratagene) (pICP07 and pICP16).

Likewise, the internal NdeI fragment and a HindIII fragment partially comprising the PvuII fragment were subcloned to give the pICN22 and pICH42 subclones, respectively.

To locate the ι-carrageenase gene, libraries were constructed from the pICP07 and pICP16 subclones in phagemid pbluescript with the aid of the exonuclease III of *E. coli*, using the "ExoIII" kit from Pharmacia.

The subclones and the ExoIII clones obtained were plated onto Zd medium solidified with ι-carrageenan.

Only the pICP16 and pICP07 clones and the ExoIII pICP074 and pICP0712 clones (obtained by degradation with ExoIII for 4 minutes and 12 minutes, respectively, from the pICP07 clone) are ι-carrageenase-positive.

2. Cloning from *Alteromonas fortis*

The DNA of the pIP1 and pIP2 clones showed inserts of 10.45 kb and 4.125 kb respectively, having a common fragment of 3 kb. These clones showed a positive ι-carrageenase activity. Different fragments were subcloned and plated as described above. However, none of the subclones obtained proved to be ι-carrageenase-positive.

SECTION 2: Determination of the nucleotide sequences of the genes coding for the ι-carrageenases of *Cytophaga drobachiensis* and *Alteromonas fortis*

1. Sequence of the *Cytophaga drobachiensis* gene

Plasmid pICP0712 was used to determine the nucleotide sequence of the gene responsible for the ι-carrageenase activity of *C. drobachiensis* [SEQ ID No. 3].

This nucleotide sequence is composed of 1837 bp. Translation of the six reading frames revealed only one open frame, called cgiA. The potential initiation codon is situated 333 bp beyond the 5'P end of the sequence.

The protein sequence [SEQ ID No. 4] deduced from the sequence of cgiA is composed of 391 amino acids, corresponding to a theoretical molecular weight of 53.4 kDa. The hydropathic profile of this protein shows a hydrophobic region covering the first 24 amino acids. The presence of a positively charged amino acid (Lys) followed by a hydrophobic block and then by a polar segment of six amino acids suggests that this domain could be a signal peptide. According to the analyses performed by the method of Von Heijne [J. Mol. Biol. 184 : 99–105 (1985)], the signal peptidase would cleave between valine ($Val^{24}$) and threonine ($Thr^{25}$). The mature protein devoid of its signal peptide would have a theoretical molecular weight of 50.7 kDa. The identity of the cgiA gene was confirmed by determination of the amino acids at the $NH_2$ end of the partially purified protein. The sequence obtained matches the one deduced from the nucleotide sequence. The first amino acid is situated 14 residues from the $NH_2$ end generated by the signal peptidase. As the presence of the two prolines following the amino acids determined by microsequencing had slightly disturbed the order of appearance of the N-terminal residues, the sequence of an internal oligopeptide, purified by HPLC after cleavage with trypsin, was established. The sequence $NH_2$ATYKCOOH obtained is situated near the C-terminal end of the iotase (residues 396 to 399).

2. Sequence of the *Alteromonas fortis* gene

Plasmids pIHP15 and pIHPX17, subcloned from pIP1 and pIP2, were used to determine the nucleotide sequence of the gene responsible for the ι-carrageenase activity of *Alteromonas fortis*, SEQ ID No. 1. The 2085 bp fragment contains a single open reading frame of 1473 bp, called cgiA. The sequence situated upstream of the initiation codon ($ATG^{211}$) is not a coding sequence.

The protein sequence deduced from the sequence of the *A. fortis* ι-carrageenase gene [SEQ ID No. 2] consists of 491 amino acids, corresponding to a theoretical molecular weight of 54.802 kDa. In the present case, again, the N-terminal part of the protein exhibits a high hydrophobicity, suggesting that this domain could be a signal peptide; the hypothetical cleavage site would be situated between glycine ($Gly^{26}$) and alanine ($Ala^{27}$). The mature protein devoid of its signal peptide would have a theoretical molecular weight of 51.95 kDa, corresponding to a value similar to the molecular weight obtained with the protein purified by SDS-PAGE, namely 57 kDa.

SECTION 3: Comparison of the protein sequences of the ι-carrageenases of *Cytophaga drobachiensis* and *Alteromonas fortis*

After removal of the signal peptide from each sequence, it could be seen that the sequence of the ι-carrageenase of *C. drobachiensis* has similarities to that of the ι-carrageenase of *A. fortis*.

In fact, the two sequences of iota-carrageenase have a similarity of 43.2% over the whole of the linear sequence alignment. This similarity is particularly high (57.8%) between amino acids 164 and 311 (numbering of the iota-carrageenase of *Alteromonas fortis* (FIG. 1)).

At the same time, an HCA analysis showed that the HCA score between the two proteins is 82% over a domain of 293 amino acids and reaches 90.5% in the case of said domain 164–311 (FIG. 2).

No significant similarity to other polysaccharidases known hitherto could be demonstrated.

These two enzymes therefore constitute a novel family of glycosyl hydrolases.

EXAMPLE II

The Kappa-carrageenases of *Alteromonas carrageenovora* and *Cytophaga drobachiensis*

SECTION 1: Cloning of the kappa-carrageenase genes

*Alteromonas carrageenovora* ATCC 43555 was obtained from the American Type Culture Collection. The strains *A. carrageenovora* and *C. drobachiensis* were cultivated under conditions identical to those mentioned in section 1 of Example I.

Likewise, genome libraries were constructed using the strain *Escherichia coli* DH5α and plasmid vector pAT153.

1. Cloning from *Alteromonas carrageenovora*

The preparation of this gene is described in detail by T. Barbeyron in the thesis cited above (cf. Example 1) and in Gene 139, 105–109 (1994).

From the genome library of *Alteromonas carrageenovora*, 4 *E. coli* clones, called K1 to K4, were capable of hydrolyzing kappa-carrageenan.

Plasmids pKA1 to pKA4 were purified from the four independent clones and mapped with the aid of the restriction endonucleases BamHI, DraI, EcoRI, HindIII, MluI, PstI, PvuII, SalI, SspI, XbaI and XhoI.

The presence of a 2.2 kb DraI-HindIII fragment was noted in each plasmid.

This common fragment, which is the whole insert of plasmid pKA3, was sequenced in its entirety from plasmid pKA3.

2. Cloning from *Cytophaga drobachiensis*

From the genome library of *C. drobachiensis*, five *E. coli* clones, called pKC1 to pKC5, were capable of hollowing out a hole in the substrate. The plasmids isolated and purified from said clones were mapped with restriction endonucleases.

Internal fragments of 1100 bp and 600 bp respectively were subcloned from pKC1 in phagemid pbluescript and were called pKCE11 and pKCN6.

Plasmids pKC1, pKCE11 and pKCN6 were used to determine the nucleotide sequence of the kappa-carrageenase gene.

SECTION 2: Determination of the sequences of the genes coding for the kappa-carrageenases of *Alteromonas carrageenovora* and *Cytophaga drobachiensis*

1. Sequence of the *Alteromonas carrageenovora* gene

The number of nucleotides in the pKA3 insert is 2180 bp. Translation in the six reading frames reveals the presence of three open frames, only one of which is complete; this one separates the other two, which are only partial. All three of them are located on the same DNA strand. The second open frame, called cgkA, read in the third reading frame, contains 1191 bp [SEQ ID No. 5].

The translation product of the cgkA gene corresponds to a protein of 397 amino acids with a theoretical molecular weight of 44,212 Da (SEQ ID No. 6). The hydropathic profile of this protein shows a highly hydrophobic domain, extending over 25 amino acids, at the N-terminal end. This domain comprises a positively charged amino acid (Lys) followed by a segment rich in hydrophobic amino acids and then by three polar amino acids. These results suggest that a signal peptide is involved. The N-terminal sequence of the protein purified from the culture supernatant was determined, thereby confirming the identity of the gene. These results indicate that the signal peptidase cleaves the protein between residues 25 and 26, which is consistent with Von Heijne's rule (−3, −1). The mature protein therefore has a theoretical molecular weight of 41.6 kDa.

2. Sequence of the *Cytophaga drobachiensis* gene

The pKC1 insert of 4425 bp contains a single open reading frame of 1635 bp, called cgkA (SEQ ID No. 7).

The protein translated from the kappa-carrageenase gene is a protein comprising 545 amino acids with a molecular weight of 61.466 kDa [SEQ ID No. 8].

The hydropathic profile of this protein shows a highly hydrophobic domain at the N-terminal end, suggesting that a signal peptide is involved.

According to Von Heijne's rule (−3, −1), the cleavage site of the signal peptidase should be situated between threonine and serine in positions 35 and 36 respectively, with the codon ATG$^{875}$ as the initiation codon.

The molecular weight of the protein, calculated after removal of the signal peptide, is 57.4 kDa, which is greater than the molecular weight determined for the purified extracellular κ-carrageenase, namely 40.0 kDa.

SECTION 3: Comparison of the protein sequences of the κ-carrageenases of *Alteromonas carrageenovora* and *Cytophaga drobachiensis*

The κ-carrageenase of *C. drobachiensis* has a similarity of 36.1% with the κ-carrageenase of *Alteromonas carrageenovora* over the whole of the linear sequence alignment.

Figure 3:
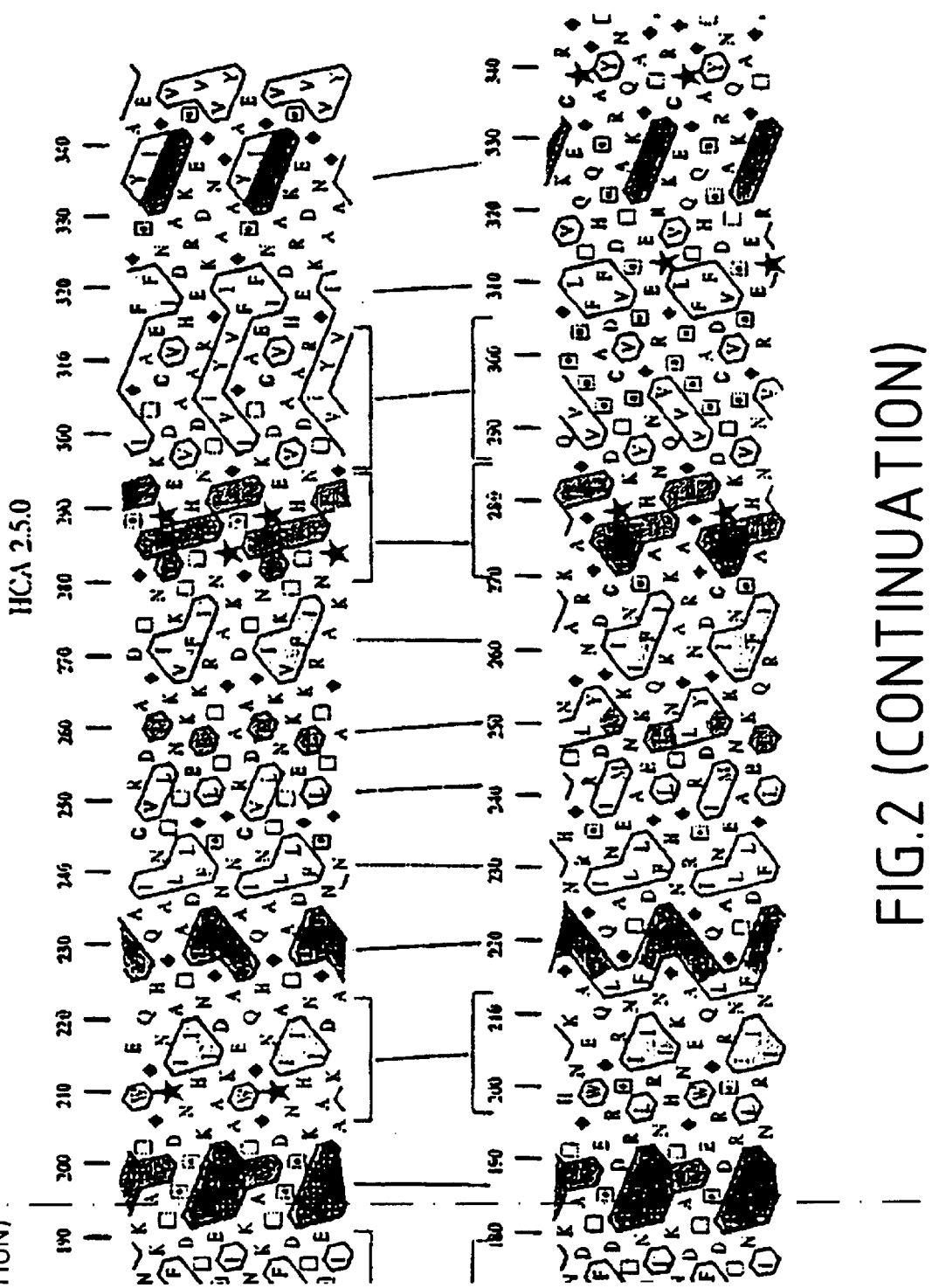
FIG. 3: The maximum similarity alignment, according to the method of Needleman and Wunsch, 1970, J. Mol. Biol. 48, 443–453, of the amino acid sequence of the kappa-carrageenase of *Alteromonas carrageenovora* SEQ ID NO: 6 (top part) and *Cytophaga drobachiensis* SEQ ID No: 8 (bottom part).

This similarity is particularly high between amino acids 117 and 262 (51.8%) (numbering of the κ-carrageenase of *Alteromonas carrageenovora*) (FIG. 3).

As previously, this similarity is substantiated by HCA analysis, which shows an HCA score between the two proteins of 75.4% over said domain of 145 amino acids (FIG. 4).

HCA analysis also shows that these two proteins belong to family 16 of glycosyl hydrolases, which includes endoxyglucan transferases (XET), laminarinases, lichenases and agarases. In fact, the HCA score of the two kappa-carrageenases is 67.5% with XET, 67.6% with laminarinases, 73.7% with lichenases and 71.5% with agarases.

What is claimed is:

1. An isolated nucleic acid molecule comprising a nucleic acid sequence encoding a protein having glycosyl hydrolase activity, wherein the nucleic acid sequence is selected from the group consisting of
   (a) a nucleic acid sequence that is SEQ ID NO: 1;
   (b) a nucleic acid sequence encoding a protein comprising the amino acid sequence of SEQ ID NO: 2;
   (c) a nucleic acid sequence that is SEQ ID NO: 3;
   (d) a nucleic acid sequence encoding a protein comprising the amino acid sequence of SEQ ID NO: 4; and
   (e) a nucleic acid sequence that is degenerate as a result of the genetic code to the nucleic acid sequence of (a), (b), (c) or (d).

2. An isolated nucleic acid molecule according to claim 1, wherein the glycosyl hydrolase has a hydrophobic cluster analysis (HCA) score with the iota-carrageenase of *Alteromonas fortis* which is greater than or equal to 65% over the domain extending between amino acids 164 and 311 of the amino acid sequence of *Alteromonas fortis* that is SEQ ID NO: 2.

3. An isolated nucleic acid molecule according to claim 2, wherein the HCA score is greater than or equal to 70%.

4. An isolated nucleic acid molecule according to claim 2, wherein the HCA score is greater than or equal to 75%.

5. A vector comprising a nucleic acid molecule according to claim 1.

6. A host cell genetically modified with a nucleic acid molecule according to claim 1 or with a vector comprising said nucleic acid molecule.

7. A method of producing a protein having glycosyl hydrolase activity, the method comprising:
   (a) obtaining the host cell of claim 6; and
   (b) growing the host cell under conditions and for a time sufficient to produce the protein.

* * * * *

SEQUENCE LISTING (1) GENERAL INFORMATION:

(iii) NUMBER OF SEQUENCES: 8

(2) INFORMATION FOR SEQ ID NO: 1:

(i) SEQUENCE CHARACTERISTICS:
       (A) LENGTH: 2085 base pairs
       (B) TYPE: nucleic acid
       (C) STRANDEDNESS: single
       (D) TOPOLOGY: linear (ii) MOLECULE TYPE: DNA (genomic)

(iii) HYPOTHETICAL: NO (ix) FEATURE:
       (A) NAME/KEY: CDS
       (B) LOCATION:join(211..1683, 1880..2083)

(xi) SEQUENCE DESCRIPTION: SEQ ID NO: 1:

```
AAGCTTTCCG ATTCTATCAT CGAAGTCATA GGAGTGGGTA AACAAAAAAG CATGAAACTA        60

GCTTTTTAAA ATACAGACTT TCAATATAGG TCGCACACAA TATTAACGAA TAAATAAGCA       120

AATCATATAC ATAATCATTG CTTTAAATAT GTTTTAATAC AGATATAAAC ATAGTATGTT       180

TGTGTTTTTG GTATCTATCG GAGTGAAAAC ATG CGC TTA TAT TTT AGA AAG TTG       234
                                  Met Arg Leu Tyr Phe Arg Lys Leu
                                   1               5

TGG TTA ACA AAT TTA TTT TTA GGC GGA GCA CTG GCC TCT TCA GCT GCG        282
Trp Leu Thr Asn Leu Phe Leu Gly Gly Ala Leu Ala Ser Ser Ala Ala
     10              15                  20

ATA GGG GCT GTC TCC CCC AAG ACT TAT AAG GAC GCA GAT TTT TAT GTT        330
Ile Gly Ala Val Ser Pro Lys Thr Tyr Lys Asp Ala Asp Phe Tyr Val
 25              30                  35                  40

GCC CCT ACT CAA CAA GAT GTT AAC TAT GAT TTA GTT GAT GAT TTT GGC        378
Ala Pro Thr Gln Gln Asp Val Asn Tyr Asp Leu Val Asp Asp Phe Gly
                 45                  50                  55

GCT AAT GGA AAC GAC ACT AGT GAT GAC AGT AAT GCT TTA CAA AGA GCA        426
Ala Asn Gly Asn Asp Thr Ser Asp Asp Ser Asn Ala Leu Gln Arg Ala
                     60                  65                  70

ATT AAT GCT ATT AGT AGA AAA CCG AAT GGG GGC ACT TTA CTA ATA CCG        474
Ile Asn Ala Ile Ser Arg Lys Pro Asn Gly Gly Thr Leu Leu Ile Pro
         75                  80                  85

AAT GGA ACT TAC CAT TTC CTC GGC ATA CAG ATG AAG TCG AAC GTA CAC        522
Asn Gly Thr Tyr His Phe Leu Gly Ile Gln Met Lys Ser Asn Val His
     90                  95                 100

ATC CGT GTT GAG AGT GAC GTG ATA ATC AAG CCA ACG TGG AAT GGG GAT        570
Ile Arg Val Glu Ser Asp Val Ile Ile Lys Pro Thr Trp Asn Gly Asp
105                 110                 115                 120

GGC AAA AAC CAC CGA CTA TTT GAA GTT GGC GTA AAC AAT ATT GTA AGA        618
Gly Lys Asn His Arg Leu Phe Glu Val Gly Val Asn Asn Ile Val Arg
                125                 130                 135

AAC TTC AGC TTT CAA GGG TTA GGA AAC GGT TTT TTG GTG GAT TTT AAA        666
Asn Phe Ser Phe Gln Gly Leu Gly Asn Gly Phe Leu Val Asp Phe Lys
                    140                 145                 150

GAT TCT CGC GAC AAA AAC TTA GCT GTT TTT AAG TTA GGC GAT GTT AGA        714
Asp Ser Arg Asp Lys Asn Leu Ala Val Phe Lys Leu Gly Asp Val Arg
            155                 160                 165

AAT TAC AAA ATT TCC AAT TTT ACC ATT GAT GAT AAT AAA ACG ATA TTT        762
Asn Tyr Lys Ile Ser Asn Phe Thr Ile Asp Asp Asn Lys Thr Ile Phe
        170                 175                 180
```

```
GCC TCA ATT TTA GTG GAC GTA ACA GAA CGT AAT GGG CGG TTA CAT TGG       810
Ala Ser Ile Leu Val Asp Val Thr Glu Arg Asn Gly Arg Leu His Trp
185                 190                 195                 200

TCG CGT AAT GGA ATT ATC GAA AGA ATA AAA CAA AAT AAC GCT TTG TTC       858
Ser Arg Asn Gly Ile Ile Glu Arg Ile Lys Gln Asn Asn Ala Leu Phe
            205                 210                 215

GGC TAC GGC CTT ATT CAA ACC TAT GGC GCA GAT AAT ATT TTG TTT AGG       906
Gly Tyr Gly Leu Ile Gln Thr Tyr Gly Ala Asp Asn Ile Leu Phe Arg
                220                 225                 230

AAC CTC CAT TCG GAA GGC GGA ATT GCG TTA CGG ATG GAA ACT GAC AAC       954
Asn Leu His Ser Glu Gly Gly Ile Ala Leu Arg Met Glu Thr Asp Asn
            235                 240                 245

TTA CTT ATG AAA AAT TAT AAG CAA GGC GGA ATA AGA AAC ATC TTT GCT      1002
Leu Leu Met Lys Asn Tyr Lys Gln Gly Gly Ile Arg Asn Ile Phe Ala
250                 255                 260

GAT AAT ATC AGA TGT AGC AAA GGA CTT GCG GCG GTC ATG TTT GGC CCA      1050
Asp Asn Ile Arg Cys Ser Lys Gly Leu Ala Ala Val Met Phe Gly Pro
265                 270                 275                 280

CAT TTT ATG AAG AAT GGA GAT GTG CAA GTG ACC AAT GTC AGC TCA GTT      1098
His Phe Met Lys Asn Gly Asp Val Gln Val Thr Asn Val Ser Ser Val
                285                 290                 295

AGT TGC GGT TCG GCT GTA CGA AGT GAT AGT GGA TTT GTC GAA CTC TTT      1146
Ser Cys Gly Ser Ala Val Arg Ser Asp Ser Gly Phe Val Glu Leu Phe
            300                 305                 310

AGC CCG ACA GAC GAA GTA CAT ACG CGT CAA AGT TGG AAA CAA GCC GTT      1194
Ser Pro Thr Asp Glu Val His Thr Arg Gln Ser Trp Lys Gln Ala Val
                315                 320                 325

GAA AGT AAA TTG GGC CGA GGG TGT GCG CAA ACC CCT TAT GCT AGA GGT      1242
Glu Ser Lys Leu Gly Arg Gly Cys Ala Gln Thr Pro Tyr Ala Arg Gly
330                 335                 340

AAT GGT GGT ACA CGG TGG GCG GCT CGC GTA ACA CAA AAA GAC GCG TGT      1290
Asn Gly Gly Thr Arg Trp Ala Ala Arg Val Thr Gln Lys Asp Ala Cys
345                 350                 355                 360

TTA GAT AAA GCA AAA CTG GAA TAT GGA ATA GAG CCT GGT TCA TTT GGC      1338
Leu Asp Lys Ala Lys Leu Glu Tyr Gly Ile Glu Pro Gly Ser Phe Gly
                365                 370                 375

ACG GTT AAA GTC TTT GAT GTT ACA GCG CGT TTT GGT TAT AAC GCA GAT      1386
Thr Val Lys Val Phe Asp Val Thr Ala Arg Phe Gly Tyr Asn Ala Asp
            380                 385                 390

CTT AAA CAG GAC CAG CTA GAC TAC TTT TCT ACA TCC AAC CCT ATG TGC      1434
Leu Lys Gln Asp Gln Leu Asp Tyr Phe Ser Thr Ser Asn Pro Met Cys
                395                 400                 405

AAG CGT GTA TGC CTT CCT ACA AAA GAA CAA TGG AGT AAG CAA GGC CAA      1482
Lys Arg Val Cys Leu Pro Thr Lys Glu Gln Trp Ser Lys Gln Gly Gln
410                 415                 420

ATT TAC ATT GGT CCG TCA TTA GCT GCA GTA ATT GAT ACC ACA CCT GAA      1530
Ile Tyr Ile Gly Pro Ser Leu Ala Ala Val Ile Asp Thr Thr Pro Glu
425                 430                 435                 440

ACT TCA AAA TAC GAT TAT GAT GTG AAA ACT TTT AAC GTC AAA AGA ATA      1578
Thr Ser Lys Tyr Asp Tyr Asp Val Lys Thr Phe Asn Val Lys Arg Ile
                445                 450                 455

AAT TTT CCT GTA AAT TCA CAC AAG ACT ATC GAC ACG AAT ACT GAA AGT      1626
Asn Phe Pro Val Asn Ser His Lys Thr Ile Asp Thr Asn Thr Glu Ser
            460                 465                 470

AGC CGT GTC TGC AAT TAT TAC GGT ATG TCC GAA TGC TCC AGC AGT CGA      1674
Ser Arg Val Cys Asn Tyr Tyr Gly Met Ser Glu Cys Ser Ser Ser Arg
                475                 480                 485

TGG GAG CGA TAGATTAAGC CGCTATATTC ATTTACTAGG TAAAACTTCA              1723
Trp Glu Arg
```

```
   490
AGCCGCATTC GAAGAACTAT CGAACGCGGC TTTTTTGTTA AGAGCGCCTA TGACTCAGTA   1783

TATTTTGTAT AAATATAATT TTACATCTTG TTAAAGTAAA CATCATATGT TTATATAGGT   1843

GCAATCTAAT TTGTTAATAT AGTGTTGGAG ATAGGT ATG AAA GGT GTT TCT ACG     1897
                                        Met Lys Gly Val Ser Thr
                                                            495

AAA AAT GCT CTT TTA TTT GCA GGC TTT TCG TTA AGT CTA GTT GCA CAG    1945
Lys Asn Ala Leu Leu Phe Ala Gly Phe Ser Leu Ser Leu Val Ala Gln
        500                 505                 510

TCA GTT AGT GCA CAA GAA GCA AAA CAG CCT GAA AAA GAA GAA AAA GAT    1993
Ser Val Ser Ala Gln Glu Ala Lys Gln Pro Glu Lys Glu Glu Lys Asp
        515                 520                 525

GTT GAG GTG ATT TTG GTA TCG GCA CAA AAG CGT GAG CAA GCG CTT AAA    2041
Val Glu Val Ile Leu Val Ser Ala Gln Lys Arg Glu Gln Ala Leu Lys
530                 535                 540                 545

GAA GTG CCT GTA TCA ATT GAA GTT ATT CAA GGC GAC CTT CTA GA         2085
Glu Val Pro Val Ser Ile Glu Val Ile Gln Gly Asp Leu Leu
                550                 555
```

(2) INFORMATION FOR SEQ ID NO: 2:

(i) SEQUENCE CHARACTERISTICS:
        (A) LENGTH: 559 amino acids
        (B) TYPE: amino acid
        (D) TOPOLOGY: linear (ii) MOLECULE TYPE: protein (xi) SEQUENCE DESCRIPTION: SEQ ID NO: 2:

```
Met Arg Leu Tyr Phe Arg Lys Leu Trp Leu Thr Asn Leu Phe Leu Gly
1               5                   10                  15

Gly Ala Leu Ala Ser Ser Ala Ala Ile Gly Ala Val Ser Pro Lys Thr
            20                  25                  30

Tyr Lys Asp Ala Asp Phe Tyr Val Ala Pro Thr Gln Gln Asp Val Asn
        35                  40                  45

Tyr Asp Leu Val Asp Asp Phe Gly Ala Asn Gly Asn Asp Thr Ser Asp
    50                  55                  60

Asp Ser Asn Ala Leu Gln Arg Ala Ile Asn Ala Ile Ser Arg Lys Pro
65                  70                  75                  80

Asn Gly Gly Thr Leu Leu Ile Pro Asn Gly Thr Tyr His Phe Leu Gly
                85                  90                  95

Ile Gln Met Lys Ser Asn Val His Ile Arg Val Glu Ser Asp Val Ile
            100                 105                 110

Ile Lys Pro Thr Trp Asn Gly Asp Gly Lys Asn His Arg Leu Phe Glu
        115                 120                 125

Val Gly Val Asn Asn Ile Val Arg Asn Phe Ser Phe Gln Gly Leu Gly
    130                 135                 140

Asn Gly Phe Leu Val Asp Phe Lys Asp Ser Arg Asp Lys Asn Leu Ala
145                 150                 155                 160

Val Phe Lys Leu Gly Asp Val Arg Asn Tyr Lys Ile Ser Asn Phe Thr
                165                 170                 175

Ile Asp Asp Asn Lys Thr Ile Phe Ala Ser Ile Leu Val Asp Val Thr
            180                 185                 190

Glu Arg Asn Gly Arg Leu His Trp Ser Arg Asn Gly Ile Ile Glu Arg
        195                 200                 205

Ile Lys Gln Asn Asn Ala Leu Phe Gly Tyr Gly Leu Ile Gln Thr Tyr
    210                 215                 220
```

```
Gly Ala Asp Asn Ile Leu Phe Arg Asn Leu His Ser Glu Gly Gly Ile
225                 230                 235                 240

Ala Leu Arg Met Glu Thr Asp Asn Leu Leu Met Lys Asn Tyr Lys Gln
            245                 250                 255

Gly Gly Ile Arg Asn Ile Phe Ala Asp Asn Ile Arg Cys Ser Lys Gly
            260                 265                 270

Leu Ala Ala Val Met Phe Gly Pro His Phe Met Lys Asn Gly Asp Val
        275                 280                 285

Gln Val Thr Asn Val Ser Ser Val Ser Cys Gly Ser Ala Val Arg Ser
290                 295                 300

Asp Ser Gly Phe Val Glu Leu Phe Ser Pro Thr Asp Glu Val His Thr
305                 310                 315                 320

Arg Gln Ser Trp Lys Gln Ala Val Glu Ser Lys Leu Gly Arg Gly Cys
            325                 330                 335

Ala Gln Thr Pro Tyr Ala Arg Gly Asn Gly Gly Thr Arg Trp Ala Ala
            340                 345                 350

Arg Val Thr Gln Lys Asp Ala Cys Leu Asp Lys Ala Lys Leu Glu Tyr
            355                 360                 365

Gly Ile Glu Pro Gly Ser Phe Gly Thr Val Lys Val Phe Asp Val Thr
    370                 375                 380

Ala Arg Phe Gly Tyr Asn Ala Asp Leu Lys Gln Asp Gln Leu Asp Tyr
385                 390                 395                 400

Phe Ser Thr Ser Asn Pro Met Cys Lys Arg Val Cys Leu Pro Thr Lys
                405                 410                 415

Glu Gln Trp Ser Lys Gln Gly Gln Ile Tyr Ile Gly Pro Ser Leu Ala
            420                 425                 430

Ala Val Ile Asp Thr Thr Pro Glu Thr Ser Lys Tyr Asp Tyr Asp Val
            435                 440                 445

Lys Thr Phe Asn Val Lys Arg Ile Asn Phe Pro Val Asn Ser His Lys
    450                 455                 460

Thr Ile Asp Thr Asn Thr Glu Ser Ser Arg Val Cys Asn Tyr Tyr Gly
465                 470                 475                 480

Met Ser Glu Cys Ser Ser Ser Arg Trp Glu Arg Met Lys Gly Val Ser
            485                 490                 495

Thr Lys Asn Ala Leu Leu Phe Ala Gly Phe Ser Leu Ser Leu Val Ala
            500                 505                 510

Gln Ser Val Ser Ala Gln Glu Ala Lys Gln Pro Glu Lys Glu Lys Lys
            515                 520                 525

Asp Val Glu Val Ile Leu Val Ser Ala Gln Lys Arg Glu Gln Ala Leu
530                 535                 540

Lys Glu Val Pro Val Ser Ile Glu Val Ile Gln Gly Asp Leu Leu
545                 550                 555

(2) INFORMATION FOR SEQ ID NO: 3:

(i) SEQUENCE CHARACTERISTICS:
        (A) LENGTH: 1997 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (ix) FEATURE:
        (A) NAME/KEY: CDS
```

(B) LOCATION:join(333..1805, 1866..1997)

(xi) SEQUENCE DESCRIPTION: SEQ ID NO: 3:

```
CCCTAAAAAC TATTCTTCAT ACCCTTTGAT GTATACGTTT AAACTATAGG GAGTTAATCT      60

GGTTTTGGTG CAATTCTAGT TTAATAAATG AAGCCTTCTT TTTTGACTTA CATTTTATTA     120

ACCTCTTGAA TTCTTGGGGC TTGCTAATTA TAAAATACTT AATATCAGGT GGTTGTGTAA     180

AAGAGGTGGA AGGGTATAGG ACCGTTACTT ATAATTGGCC CCTGTCGGAA GGGGGGTTAA     240

AGGTAAAATA GTGTTTAAGT GTATTAATTA ACTTCTATAT AAGTAGGAAA ATACACTATA     300

TATTGCGACA TTATTAACCT TAAATTCTTA CA ATG AAA TTA CAA TTT AAA CCT      353
                                   Met Lys Leu Gln Phe Lys Pro
                                     1               5
```

```
GTT TAT TTA GCG TCA ATT GCC ATA ATG GCA ATA GGA TGC ACC AAA GAA      401
Val Tyr Leu Ala Ser Ile Ala Ile Met Ala Ile Gly Cys Thr Lys Glu
         10                  15                  20

GTG ACG GAA AAC GAT ACC TCC GAA ATT TCG GAA GTT CCA ACT GAA TTG      449
Val Thr Glu Asn Asp Thr Ser Glu Ile Ser Glu Val Pro Thr Glu Leu
     25                  30                  35

AGG GCC GCG GCT TCT TCA TTT TAT ACC CCA CCG GGT CAG AAT GTA CGG      497
Arg Ala Ala Ala Ser Ser Phe Tyr Thr Pro Pro Gly Gln Asn Val Arg
 40                  45                  50                  55

GCC AAT AAA AAA AAC CTG GTC ACG GAT TAC GGT GTT AAC CAC AAT GAT      545
Ala Asn Lys Lys Asn Leu Val Thr Asp Tyr Gly Val Asn His Asn Asp
                 60                  65                  70

CAG AAC GAT GAT AGT AGC AAA TTA AAC CTG GCT ATC AAA GAT TTA TCG      593
Gln Asn Asp Asp Ser Ser Lys Leu Asn Leu Ala Ile Lys Asp Leu Ser
             75                  80                  85

GAT ACC GGT GGT ATA CTG ACC CTT CCT AAG GGA AAG TAC TAT TTG ACC      641
Asp Thr Gly Gly Ile Leu Thr Leu Pro Lys Gly Lys Tyr Tyr Leu Thr
         90                  95                 100

AAA ATT AGA ATG CGC TCT AAT GTA CAT CTT GAA ATA GAA AAG GGA ACG      689
Lys Ile Arg Met Arg Ser Asn Val His Leu Glu Ile Glu Lys Gly Thr
    105                 110                 115

GTA ATC TAT CCG ACC AAG GGG TTG ACT CCT GCG AAG AAT CAC AGA ATT      737
Val Ile Tyr Pro Thr Lys Gly Leu Thr Pro Ala Lys Asn His Arg Ile
120                 125                 130                 135

TTT GAT TTT GCC AGT AAA ACA GAG GAA AAA ATA GAA AAC GCC AGT ATA      785
Phe Asp Phe Ala Ser Lys Thr Glu Glu Lys Ile Glu Asn Ala Ser Ile
                140                 145                 150

GTG GGT AAA GGA GGT AAG TTT ATA GTA GAC CTA AGA GGC AAC AGT TCT      833
Val Gly Lys Gly Gly Lys Phe Ile Val Asp Leu Arg Gly Asn Ser Ser
            155                 160                 165

AAA AAC CAA ATT GTA GCC GAT GTT GGT AAC GTA ACC AAC TTT AAA ATA      881
Lys Asn Gln Ile Val Ala Asp Val Gly Asn Val Thr Asn Phe Lys Ile
        170                 175                 180

TCG AAT TTT ACG ATC AAG GAT GAA AAA ACC ATC TTT GCT TCG ATA TTG      929
Ser Asn Phe Thr Ile Lys Asp Glu Lys Thr Ile Phe Ala Ser Ile Leu
    185                 190                 195

GTA AGC TTT ACG GAT AAG GCA GGC AAT GCT TGG CCA CAT AAA GGT ATT      977
Val Ser Phe Thr Asp Lys Ala Gly Asn Ala Trp Pro His Lys Gly Ile
200                 205                 210                 215

ATT GAG AAT ATA GAC CAG GCG AAT GCC CAT ACG GGA TAT GGC CTC ATA     1025
Ile Glu Asn Ile Asp Gln Ala Asn Ala His Thr Gly Tyr Gly Leu Ile
                220                 225                 230

CAG GCG TAC GCG GCA GAT AAC ATT CTG TTC AAC AAT CTA AGT TGT ACG     1073
Gln Ala Tyr Ala Ala Asp Asn Ile Leu Phe Asn Asn Leu Ser Cys Thr
            235                 240                 245

GGC GGG GTA ACC TTG CGT TTA GAA ACC GAC AAC CTC GCT ATG AAA ACC     1121
Gly Gly Val Thr Leu Arg Leu Glu Thr Asp Asn Leu Ala Met Lys Thr
```

```
Gly Gly Val Thr Leu Arg Leu Glu Thr Asp Asn Leu Ala Met Lys Thr
            250                 255                 260

GCT AAA AAA GGG GGG GTA AGG GAT ATT TTT GCC ACA AAG ATC AAG AAT      1169
Ala Lys Lys Gly Gly Val Arg Asp Ile Phe Ala Thr Lys Ile Lys Asn
        265                 270                 275

ACC AAT GGC TTG ACC CCG GTA ATG TTC TCT CCC CAT TTT ATG GAA AAC      1217
Thr Asn Gly Leu Thr Pro Val Met Phe Ser Pro His Phe Met Glu Asn
280                 285                 290                 295

GGT AAA GTG ACC ATA GAT GAT GTA ACC GCC ATC GGT TGT GCA TAT GCC      1265
Gly Lys Val Thr Ile Asp Asp Val Thr Ala Ile Gly Cys Ala Tyr Ala
                300                 305                 310

GTA CGT GTA GAG CAC GGT TTT ATA GAG ATT TTC GAT AAG GGG AAT AGG      1313
Val Arg Val Glu His Gly Phe Ile Glu Ile Phe Asp Lys Gly Asn Arg
            315                 320                 325

GCA AGT GCC GAC GCT TTC AAG AAC TAT ATT GAA GGT ATT CTA GGA GCT      1361
Ala Ser Ala Asp Ala Phe Lys Asn Tyr Ile Glu Gly Ile Leu Gly Ala
        330                 335                 340

GGC TCG GTA GAA GTC GTG TAC AAA CGT AAT AAC GGA AGA ACA TGG GCG      1409
Gly Ser Val Glu Val Val Tyr Lys Arg Asn Asn Gly Arg Thr Trp Ala
    345                 350                 355

GCA CGT ATC GCA AAC GAC TTT AAC GAA GCG GCG TAT AAC CAC TCC AAT      1457
Ala Arg Ile Ala Asn Asp Phe Asn Glu Ala Ala Tyr Asn His Ser Asn
360                 365                 370                 375

CCT GCC GTT AGC GGA ATC AAA CCA GGG AAA TTC GCC ACA TCT AAG GTA      1505
Pro Ala Val Ser Gly Ile Lys Pro Gly Lys Phe Ala Thr Ser Lys Val
                380                 385                 390

ACC AAT GTT AAG GCA ACC TAT AAG GGT ACT GGC GCC AAA CTC AAG CAG      1553
Thr Asn Val Lys Ala Thr Tyr Lys Gly Thr Gly Ala Lys Leu Lys Gln
            395                 400                 405

GCA TTC TTA TCC TAT TTA CCC TGT TCG GAA CGT TCT AAG GTT TGT CGG      1601
Ala Phe Leu Ser Tyr Leu Pro Cys Ser Glu Arg Ser Lys Val Cys Arg
        410                 415                 420

CCA GGT CCA GAT GGG TTC GAG TAT AAC GGA CCC TCC TTG GGA GTT ACC      1649
Pro Gly Pro Asp Gly Phe Glu Tyr Asn Gly Pro Ser Leu Gly Val Thr
    425                 430                 435

ATC GAT AAC ACG AAA AGG GAC AAC AGC CTT GGC AAT TAT AAC GTC AAT      1697
Ile Asp Asn Thr Lys Arg Asp Asn Ser Leu Gly Asn Tyr Asn Val Asn
440                 445                 450                 455

GTA AGC ACC TCC AGT GTT CAG GGC TTT CCC AAT AAT TAC GTT TTA AAC      1745
Val Ser Thr Ser Ser Val Gln Gly Phe Pro Asn Asn Tyr Val Leu Asn
                460                 465                 470

GTA AAG TAT AAT ACC CCT AAA GTA TGT AAC CAA AAT CTA GGT AGT ATT      1793
Val Lys Tyr Asn Thr Pro Lys Val Cys Asn Gln Asn Leu Gly Ser Ile
            475                 480                 485

ACT TCG TGT AAC TGATCACGAA ACAATTTGTA AATAAAAAGC AGCTGTCCCT          1845
Thr Ser Cys Asn
        490

TATTACGGGC GGCTGCTTTT ATG TCT TTA AGC CAT GTC GTG ATT TAT TGG        1895
                     Met Ser Leu Ser His Val Val Ile Tyr Trp
                                      495                 500

CGA CTT TTG ATA AAG GCT TGG ATT TCT TCC GGG GTA AAT ATC GGA TTG      1943
Arg Leu Leu Ile Lys Ala Trp Ile Ser Ser Gly Val Asn Ile Gly Leu
            505                 510                 515

GCC CCT TCC CTA CCG GCT ACC ATA GCT CTA TGC TCC TAT GCA CAG GCG      1991
Ala Pro Ser Leu Pro Ala Thr Ile Ala Leu Cys Ser Tyr Ala Gln Ala
        520                 525                 530

AAA TCT                                                              1997
Lys Ser
535
```

(2) INFORMATION FOR SEQ ID NO: 4:

(i) SEQUENCE CHARACTERISTICS:
        (A) LENGTH: 535 amino acids
        (B) TYPE: amino acid
        (D) TOPOLOGY: linear (ii) MOLECULE TYPE: protein (xi) SEQUENCE DESCRIPTION: SEQ ID NO: 4:

```
Met Lys Leu Gln Phe Lys Pro Val Tyr Leu Ala Ser Ile Ala Ile Met
 1               5                  10                  15

Ala Ile Gly Cys Thr Lys Glu Val Thr Glu Asn Asp Thr Ser Glu Ile
             20                  25                  30

Ser Glu Val Pro Thr Glu Leu Arg Ala Ala Ser Ser Phe Tyr Thr
         35                  40                  45

Pro Pro Gly Gln Asn Val Arg Ala Asn Lys Lys Asn Leu Val Thr Asp
         50                  55                  60

Tyr Gly Val Asn His Asn Asp Gln Asn Asp Asp Ser Ser Lys Leu Asn
 65                  70                  75                  80

Leu Ala Ile Lys Asp Leu Ser Asp Thr Gly Gly Ile Leu Thr Leu Pro
                 85                  90                  95

Lys Gly Lys Tyr Tyr Leu Thr Lys Ile Arg Met Arg Ser Asn Val His
                100                 105                 110

Leu Glu Ile Glu Lys Gly Thr Val Ile Tyr Pro Thr Lys Gly Leu Thr
                115                 120                 125

Pro Ala Lys Asn His Arg Ile Phe Asp Phe Ala Ser Lys Thr Glu Glu
                130                 135                 140

Lys Ile Glu Asn Ala Ser Ile Val Gly Lys Gly Lys Phe Ile Val
145                 150                 155                 160

Asp Leu Arg Gly Asn Ser Ser Lys Asn Gln Ile Val Ala Asp Val Gly
                165                 170                 175

Asn Val Thr Asn Phe Lys Ile Ser Asn Phe Thr Ile Lys Asp Glu Lys
                180                 185                 190

Thr Ile Phe Ala Ser Ile Leu Val Ser Phe Thr Asp Lys Ala Gly Asn
                195                 200                 205

Ala Trp Pro His Lys Gly Ile Ile Glu Asn Ile Asp Gln Ala Asn Ala
                210                 215                 220

His Thr Gly Tyr Gly Leu Ile Gln Ala Tyr Ala Ala Asp Asn Ile Leu
225                 230                 235                 240

Phe Asn Asn Leu Ser Cys Thr Gly Gly Val Thr Leu Arg Leu Glu Thr
                245                 250                 255

Asp Asn Leu Ala Met Lys Thr Ala Lys Lys Gly Gly Val Arg Asp Ile
                260                 265                 270

Phe Ala Thr Lys Ile Lys Asn Thr Asn Gly Leu Thr Pro Val Met Phe
                275                 280                 285

Ser Pro His Phe Met Glu Asn Gly Lys Val Thr Ile Asp Asp Val Thr
                290                 295                 300

Ala Ile Gly Cys Ala Tyr Ala Val Arg Val Glu His Gly Phe Ile Glu
305                 310                 315                 320

Ile Phe Asp Lys Gly Asn Arg Ala Ser Ala Asp Ala Phe Lys Asn Tyr
                325                 330                 335

Ile Glu Gly Ile Leu Gly Ala Gly Ser Val Glu Val Val Tyr Lys Arg
                340                 345                 350

Asn Asn Gly Arg Thr Trp Ala Ala Arg Ile Ala Asn Asp Phe Asn Glu
```

```
            355                 360                 365
Ala Ala Tyr Asn His Ser Asn Pro Ala Val Ser Gly Ile Lys Pro Gly
    370                 375                 380

Lys Phe Ala Thr Ser Lys Val Thr Asn Val Lys Ala Thr Tyr Lys Gly
385                 390                 395                 400

Thr Gly Ala Lys Leu Lys Gln Ala Phe Leu Ser Tyr Leu Pro Cys Ser
                405                 410                 415

Glu Arg Ser Lys Val Cys Arg Pro Gly Pro Asp Gly Phe Glu Tyr Asn
            420                 425                 430

Gly Pro Ser Leu Gly Val Thr Ile Asp Asn Thr Lys Arg Asp Asn Ser
                435                 440                 445

Leu Gly Asn Tyr Asn Val Asn Val Ser Thr Ser Val Gln Gly Phe
    450                 455                 460

Pro Asn Asn Tyr Val Leu Asn Val Lys Tyr Asn Thr Pro Lys Val Cys
465                 470                 475                 480

Asn Gln Asn Leu Gly Ser Ile Thr Ser Cys Asn Met Ser Leu Ser His
                485                 490                 495

Val Val Ile Tyr Trp Arg Leu Leu Ile Lys Ala Trp Ile Ser Ser Gly
            500                 505                 510

Val Asn Ile Gly Leu Ala Pro Ser Leu Pro Ala Thr Ile Ala Leu Cys
            515                 520                 525

Ser Tyr Ala Gln Ala Lys Ser
            530                 535
```

(2) INFORMATION FOR SEQ ID NO: 5:

(i) SEQUENCE CHARACTERISTICS:
        (A) LENGTH: 2180 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (ix) FEATURE:
        (A) NAME/KEY: CDS
        (B) LOCATION:join(1..498, 741..1931, 2009..2179)

(xi) SEQUENCE DESCRIPTION: SEQ ID NO: 5:

```
GAT CAT ATC ATT CCT TTG CAA ATT AAA AAT TCT CAA GAT AGT CAA ATA        48
Asp His Ile Ile Pro Leu Gln Ile Lys Asn Ser Gln Asp Ser Gln Ile
 1               5                  10                  15

ATT AGT TTT TTT AAA GCT GAC AAA GGG AGT GTG AGC AGG CAA GTA CAC        96
Ile Ser Phe Phe Lys Ala Asp Lys Gly Ser Val Ser Arg Gln Val His
            20                  25                  30

CCA CCT TGG CCT GTG CCT TGT AAA AGT AAA CTG CAA GAG CAA GAT AGT       144
Pro Pro Trp Pro Val Pro Cys Lys Ser Lys Leu Gln Glu Gln Asp Ser
        35                  40                  45

AGT GAG TCT AAA GAG AGT AAG GCA GAG CAA GTT AAA ATT AAC AAC TGC       192
Ser Glu Ser Lys Glu Ser Lys Ala Glu Gln Val Lys Ile Asn Asn Cys
50                  55                  60

GTT GTA CAG AAC GCA ATG CTG TAC ATA GAA AAC AAT TAT TTC AAC GAT       240
Val Val Gln Asn Ala Met Leu Tyr Ile Glu Asn Asn Tyr Phe Asn Asp
65                  70                  75                  80

ATA AAT ATA GAC ACG GTT GCT TTT TCT GTT GGC GTA AGT CGC TCT TAT       288
Ile Asn Ile Asp Thr Val Ala Phe Ser Val Gly Val Ser Arg Ser Tyr
                85                  90                  95

CTC GTT AAA CAA TTT AAG TTA GCA ACG AAT AAA ACG ATT AAT AAT AGA       336
```

```
                Leu Val Lys Gln Phe Lys Leu Ala Thr Asn Lys Thr Ile Asn Asn Arg
                                100                 105                 110

ATC ATA GAA GTA AGA ATA GAG CAG GCT AAA AAA GTA TTA CTA AAA AAA           384
Ile Ile Glu Val Arg Ile Glu Gln Ala Lys Lys Val Leu Leu Lys Lys
            115                 120                 125

TCT GTT ACA GAA ACA GCT TAT GAA GTT GGT TTT AAT AAC TCA AAC TAC           432
Ser Val Thr Glu Thr Ala Tyr Glu Val Gly Phe Asn Asn Ser Asn Tyr
        130                 135                 140

TTC GCG ACA GTT TTT AAA AAA AGA ACA AAC TAC ACG CCC AAG CAA TTT           480
Phe Ala Thr Val Phe Lys Lys Arg Thr Asn Tyr Thr Pro Lys Gln Phe
145                 150                 155                 160

AAA CGT ACT TTT TCC AGC TAAAACTACA ACTAAATAAC GATTAAAAGC                  528
Lys Arg Thr Phe Ser Ser
                165

CATTTTTAGA GAACAGTAAA ACCATTTTTT GAGGTTTGGT GTTGTATATA AATATTAAAT         588

ATCCCCACTC GCTCAGCTTT TTTTGTGCGA GTTGTGAGAA TTAGCTTAAC AGGTAAGGTT         648

TACGTATCTG TATATCTAAA CTCTTCGAAT ATAACACTGT ATCTGTTGCT GAGCTGTGGC         708

TCAGTTCACA CTAACAAAGG ATGGATAAAT AA ATG AAA CCT ATA AGT ATT GTG           761
                                   Met Lys Pro Ile Ser Ile Val
                                                       170

GCA TTC CCT ATA CCA GCT ATA AGT ATG CTT CTT TTA AGT GCA GTA TCA           809
Ala Phe Pro Ile Pro Ala Ile Ser Met Leu Leu Leu Ser Ala Val Ser
        175                 180                 185

CAA GCA GCA TCT ATG CAA CCT CCC ATC GCA AAA CCT GGT GAA ACA TGG           857
Gln Ala Ala Ser Met Gln Pro Pro Ile Ala Lys Pro Gly Glu Thr Trp
190                 195                 200                 205

ATT TTA CAA GCC AAA CGC TCT GAC GAA TTT AAC GTA AAA GAT GCG ACA           905
Ile Leu Gln Ala Lys Arg Ser Asp Glu Phe Asn Val Lys Asp Ala Thr
                210                 215                 220

AAG TGG AAC TTT CAA ACA GAA AAC TAT GGG GTA TGG TCT TGG AAA AAT           953
Lys Trp Asn Phe Gln Thr Glu Asn Tyr Gly Val Trp Ser Trp Lys Asn
            225                 230                 235

GAA AAT GCG ACA GTA TCT AAT GGC AAA CTA AAA TTA ACC ACT AAG CGA          1001
Glu Asn Ala Thr Val Ser Asn Gly Lys Leu Lys Leu Thr Thr Lys Arg
        240                 245                 250

GAA TCT CAT CAA CGT ACA TTC TGG GAT GGC TGT AAT CAG CAG CAA GTT          1049
Glu Ser His Gln Arg Thr Phe Trp Asp Gly Cys Asn Gln Gln Gln Val
255                 260                 265

GCA AAT TAC CCA CTT TAT TAT ACA TCG GGT GTC GCT AAA TCC AGA GCT          1097
Ala Asn Tyr Pro Leu Tyr Tyr Thr Ser Gly Val Ala Lys Ser Arg Ala
270                 275                 280                 285

ACA GGT AAT TAT GGC TAT TAC GAA GCT CGA ATC AAA GGA GCG AGT ACA          1145
Thr Gly Asn Tyr Gly Tyr Tyr Glu Ala Arg Ile Lys Gly Ala Ser Thr
                290                 295                 300

TTT CCT GGC GTA TCG CCT GCT TTT TGG ATG TAT AGC ACC ATT GAC CGT          1193
Phe Pro Gly Val Ser Pro Ala Phe Trp Met Tyr Ser Thr Ile Asp Arg
            305                 310                 315

TCA TTA ACG AAA GAA GGG GAT GTC CAA TAT AGC GAA ATA GAC GTA GTG          1241
Ser Leu Thr Lys Glu Gly Asp Val Gln Tyr Ser Glu Ile Asp Val Val
        320                 325                 330

GAA CTT ACT CAA AAA AGT GCA GTG AGA GAG TCT GAT CAT GAC TTA CAC          1289
Glu Leu Thr Gln Lys Ser Ala Val Arg Glu Ser Asp His Asp Leu His
335                 340                 345

AAT ATT GTA GTA AAA AAT GGA AAA CCA ACA TGG ATG CGT CCA GGG TCT          1337
Asn Ile Val Val Lys Asn Gly Lys Pro Thr Trp Met Arg Pro Gly Ser
350                 355                 360                 365

TTT CCG CAG ACA AAT CAT AAC GGA TAC CAT CTA CCT TTC GAT CCT CGA          1385
Phe Pro Gln Thr Asn His Asn Gly Tyr His Leu Pro Phe Asp Pro Arg
```

-continued

```
                     370                 375                 380
AAT GAC TTT CAC ACC TAT GGT GTC AAT GTA ACT AAA GAC AAG ATC ACT    1433
Asn Asp Phe His Thr Tyr Gly Val Asn Val Thr Lys Asp Lys Ile Thr
                385                 390                 395

TGG TAC GTA GAT GGT GAA ATT GTG GGC GAA AAG GAT AAC TTA TAC TGG    1481
Trp Tyr Val Asp Gly Glu Ile Val Gly Glu Lys Asp Asn Leu Tyr Trp
            400                 405                 410

CAT CGT CAA ATG AAT CTC ACA TTA TCA CAA GGC TTA CGC GCG CCG CAT    1529
His Arg Gln Met Asn Leu Thr Leu Ser Gln Gly Leu Arg Ala Pro His
        415                 420                 425

ACA CAA TGG AAA TGT AAT CAA TTT TAC CCA TCA GCG AAT AAA TCA GCA    1577
Thr Gln Trp Lys Cys Asn Gln Phe Tyr Pro Ser Ala Asn Lys Ser Ala
430                 435                 440                 445

GAA GGC TTC CCA ACA TCA ATG GAA GTT GAT TAT GTA AGA ACG TGG GTA    1625
Glu Gly Phe Pro Thr Ser Met Glu Val Asp Tyr Val Arg Thr Trp Val
                450                 455                 460

AAG GTG GGC AAT AAC AAC TCT GCT CCA GGC GAG GGG CAG TCA TGT CCT    1673
Lys Val Gly Asn Asn Asn Ser Ala Pro Gly Glu Gly Gln Ser Cys Pro
            465                 470                 475

AAC ACG TTT GTA GCT GTC AAT AGT GTT CAA CTA AGC GCA GCA AAA CAA    1721
Asn Thr Phe Val Ala Val Asn Ser Val Gln Leu Ser Ala Ala Lys Gln
        480                 485                 490

ACA CTT CGA AAG GGC CAA TCT ACA ACG CTA GAA AGC ACA GTT CTT CCA    1769
Thr Leu Arg Lys Gly Gln Ser Thr Thr Leu Glu Ser Thr Val Leu Pro
    495                 500                 505

AAC TGT GCA ACC AAC AAG AAA GTC ATT TAT TCA TCA AGC AAT AAA AAT    1817
Asn Cys Ala Thr Asn Lys Lys Val Ile Tyr Ser Ser Ser Asn Lys Asn
510                 515                 520                 525

GTG GCA ACT GTG AAC AGT GCT GGC GTT GTA AAA GCT AAA AAT AAA GGC    1865
Val Ala Thr Val Asn Ser Ala Gly Val Val Lys Ala Lys Asn Lys Gly
                530                 535                 540

ACT GCG ACG ATT ACG GTT AAA ACT AAA AAC AAA GGG AAA ATA GAT AAA    1913
Thr Ala Thr Ile Thr Val Lys Thr Lys Asn Lys Gly Lys Ile Asp Lys
            545                 550                 555

TTA ACC ATT GCG GTG AAT TAAGCTAACT CAAACTAGCC TCGAAGGATT          1961
Leu Thr Ile Ala Val Asn
        560

GAGGCACTTT ATTTATAGGT CTCAGGCTTC GACTTTTTGG AGGGGGT ATG AAA AAG    2017
                                                    Met Lys Lys
                                                        565

GTA AAT TTA TCC AGC AAG TGG ATA ATT AGC ATT AGT TTA CTA ATC ATT    2065
Val Asn Leu Ser Ser Lys Trp Ile Ile Ser Ile Ser Leu Leu Ile Ile
                570                 575                 580

TGT GAT TAT GTT TAT TTA ATA CGA ACA AAC GTT AAC GAG CAA GCT AAC    2113
Cys Asp Tyr Val Tyr Leu Ile Arg Thr Asn Val Asn Glu Gln Ala Asn
            585                 590                 595

GCA GAA GCT ACT GCA CAT ATG CAT TAC AAA ATA AAT AAT ACG AAA CAC    2161
Ala Glu Ala Thr Ala His Met His Tyr Lys Ile Asn Asn Thr Lys His
        600                 605                 610

TCA AAA GGA AAG CTT GAT C                                         2180
Ser Lys Gly Lys Leu Asp
615                 620
```

(2) INFORMATION FOR SEQ ID NO: 6:

(i) SEQUENCE CHARACTERISTICS:
        (A) LENGTH: 620 amino acids
        (B) TYPE: amino acid
        (D) TOPOLOGY: linear (ii) MOLECULE TYPE: protein (xi) SEQUENCE DESCRIPTION: SEQ ID NO: 6:

```
Asp His Ile Ile Pro Leu Gln Ile Lys Asn Ser Gln Asp Ser Gln Ile
 1               5                   10                  15
Ile Ser Phe Phe Lys Ala Asp Lys Gly Ser Val Ser Arg Gln Val His
             20                  25                  30
Pro Pro Trp Pro Val Pro Cys Lys Ser Lys Leu Gln Glu Gln Asp Ser
         35                  40                  45
Ser Glu Ser Lys Glu Ser Lys Ala Glu Gln Val Lys Ile Asn Asn Cys
     50                  55                  60
Val Val Gln Asn Ala Met Leu Tyr Ile Glu Asn Asn Tyr Phe Asn Asp
 65                  70                  75                  80
Ile Asn Ile Asp Thr Val Ala Phe Ser Val Gly Val Ser Arg Ser Tyr
                 85                  90                  95
Leu Val Lys Gln Phe Lys Leu Ala Thr Asn Lys Thr Ile Asn Asn Arg
            100                 105                 110
Ile Ile Glu Val Arg Ile Glu Gln Ala Lys Lys Val Leu Leu Lys Lys
        115                 120                 125
Ser Val Thr Glu Thr Ala Tyr Glu Val Gly Phe Asn Asn Ser Asn Tyr
    130                 135                 140
Phe Ala Thr Val Phe Lys Lys Arg Thr Asn Tyr Thr Pro Lys Gln Phe
145                 150                 155                 160
Lys Arg Thr Phe Ser Ser Met Lys Pro Ile Ser Ile Val Ala Phe Pro
                165                 170                 175
Ile Pro Ala Ile Ser Met Leu Leu Leu Ser Ala Val Ser Gln Ala Ala
            180                 185                 190
Ser Met Gln Pro Pro Ile Ala Lys Pro Gly Glu Thr Trp Ile Leu Gln
        195                 200                 205
Ala Lys Arg Ser Asp Glu Phe Asn Val Lys Asp Ala Thr Lys Trp Asn
    210                 215                 220
Phe Gln Thr Glu Asn Tyr Gly Val Trp Ser Trp Lys Asn Glu Asn Ala
225                 230                 235                 240
Thr Val Ser Asn Gly Lys Leu Lys Leu Thr Thr Lys Arg Glu Ser His
                245                 250                 255
Gln Arg Thr Phe Trp Asp Gly Cys Asn Gln Gln Val Ala Asn Tyr
            260                 265                 270
Pro Leu Tyr Tyr Thr Ser Gly Val Ala Lys Ser Arg Ala Thr Gly Asn
        275                 280                 285
Tyr Gly Tyr Tyr Glu Ala Arg Ile Lys Gly Ala Ser Thr Phe Pro Gly
    290                 295                 300
Val Ser Pro Ala Phe Trp Met Tyr Ser Thr Ile Asp Arg Ser Leu Thr
305                 310                 315                 320
Lys Glu Gly Asp Val Gln Tyr Ser Glu Ile Asp Val Val Glu Leu Thr
                325                 330                 335
Gln Lys Ser Ala Val Arg Glu Ser Asp His Asp Leu His Asn Ile Val
            340                 345                 350
Val Lys Asn Gly Lys Pro Thr Trp Met Arg Pro Gly Ser Phe Pro Gln
        355                 360                 365
Thr Asn His Asn Gly Tyr His Leu Pro Phe Asp Pro Arg Asn Asp Phe
    370                 375                 380
His Thr Tyr Gly Val Asn Val Thr Lys Asp Lys Ile Thr Trp Tyr Val
385                 390                 395                 400
Asp Gly Glu Ile Val Gly Glu Lys Asp Asn Leu Tyr Trp His Arg Gln
```

```
                            405                  410                  415
Met Asn Leu Thr Leu Ser Gln Gly Leu Arg Ala Pro His Thr Gln Trp
            420                  425                  430

Lys Cys Asn Gln Phe Tyr Pro Ser Ala Asn Lys Ser Ala Glu Gly Phe
            435                  440                  445

Pro Thr Ser Met Glu Val Asp Tyr Val Arg Thr Trp Val Lys Val Gly
        450                  455                  460

Asn Asn Asn Ser Ala Pro Gly Glu Gly Gln Ser Cys Pro Asn Thr Phe
465                  470                  475                  480

Val Ala Val Asn Ser Val Gln Leu Ser Ala Ala Lys Gln Thr Leu Arg
                485                  490                  495

Lys Gly Gln Ser Thr Thr Leu Glu Ser Thr Val Leu Pro Asn Cys Ala
            500                  505                  510

Thr Asn Lys Lys Val Ile Tyr Ser Ser Ser Asn Lys Asn Val Ala Thr
            515                  520                  525

Val Asn Ser Ala Gly Val Val Lys Ala Lys Asn Lys Gly Thr Ala Thr
            530                  535                  540

Ile Thr Val Lys Thr Lys Asn Lys Gly Lys Ile Asp Lys Leu Thr Ile
545                  550                  555                  560

Ala Val Asn Met Lys Lys Val Asn Leu Ser Ser Lys Trp Ile Ile Ser
                565                  570                  575

Ile Ser Leu Leu Ile Ile Cys Asp Tyr Val Tyr Leu Ile Arg Thr Asn
            580                  585                  590

Val Asn Glu Gln Ala Asn Ala Glu Ala Thr Ala His Met His Tyr Lys
            595                  600                  605

Ile Asn Asn Thr Lys His Ser Lys Gly Lys Leu Asp
        610                  615                  620

(2) INFORMATION FOR SEQ ID NO: 7:

(i) SEQUENCE CHARACTERISTICS:
        (A) LENGTH: 2600 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (ix) FEATURE:
        (A) NAME/KEY: CDS
        (B) LOCATION:875..2509

(xi) SEQUENCE DESCRIPTION: SEQ ID NO: 7:

GCCTCCGTAT TCGACAATGT TGTACGATGC TTGGCGATTC GGACTCTGTT TAAGCACTCG      60

ATTTCGTAAA GGCACTATCC ACTCATTCAT TCCGACTCAA TATTCTTTTC GACAAATGCA     120

ACCGGTTCCA TTGAAAAGGC CCTAAAAATA CAGCTTTCCC GCCCCCCATC GTAGAAGGTT     180

CCAATATGCT TCAACCCCTT TTTCAGCCTT ACTTCAGGGG TATTACTTTC ATGCCTAGGG     240

CCGCAAATAC ATTCGCTTGG ACCCAGTCAC CTATATAATT GAATACGGAA CTACCCATGG     300

CTTCCTTCCC TTTGGGAACC TATGGTACAG ACTTGCCTTT TTTAAACCGG TTACTTCAGC     360

TAATTCGCCA AGCTGGTTCC TTCATAACCT TTGGCCCGAA ACACCTTGCA AGCACATAAA     420

TCTTATCCAA TATTTTGCGG TCTCATGGGA CAAATCTATA ACAAACATTC AATTTTACCA     480

AACGTTCGGT AATAAATCTA GTCAAAAACG GGTCCGATT CATTTTAGAA GAAAGGTAAA     540

GCCCCCAAAA GAGCGGTTTA CTTGAAGATA TGATTTATAA AACACAATAA GTGACAAAGG     600
```

```
AAGATCATGG CTATAATTAG TTGAAAAAAC AGGGCTTACC ATGACATGGA GCTTTATTGA      660

AAACAGATGT CCAACAAGAA TAAAGGAGGG CCGTTCGACC GCGACGTTTA AATAAAAACA      720

TATTCCATAT CAAAATTTAA TTAAGGTTCT TTCCTACAGT ATTTATAAGA AATTACTAAA      780

ATTAGTTAGG ATAATACTAC AAAATGGTAA AATTGGATTA CTCAGATTGA ACCATAGCCT      840

CTACTTTAGT CGGCTAACAA AAACAATTAT AGTA ATG AAA AAA CCA AAT TTT          892
                                      Met Lys Lys Pro Asn Phe
                                       1               5

TAT GGC AAG ATG GGT AGA ACT GCA CTT TCA AGT CTT TTC TAC CTC TTT        940
Tyr Gly Lys Met Gly Arg Thr Ala Leu Ser Ser Leu Phe Tyr Leu Phe
             10                  15                  20

TTC CTA GGC CTT GTG TAT GGG CAA CAA CCT ACG AAG ACT TCA AAT CCG        988
Phe Leu Gly Leu Val Tyr Gly Gln Gln Pro Thr Lys Thr Ser Asn Pro
             25                  30                  35

AAC GAT CAG TGG ACC ATC AAA TGG AGT GCT TCG GAC GAA TTC AAC AAA       1036
Asn Asp Gln Trp Thr Ile Lys Trp Ser Ala Ser Asp Glu Phe Asn Lys
         40                  45                  50

AAT GAC CCC GAC TGG GCA AAA TGG ATC AAG ACA GGA AAC CTT CCG AAT       1084
Asn Asp Pro Asp Trp Ala Lys Trp Ile Lys Thr Gly Asn Leu Pro Asn
 55                  60                  65                  70

ACA TCG GCA TGG AAA TGG AAC AAT CAA AAA AAC GTA AAG ATT TCC AAC       1132
Thr Ser Ala Trp Lys Trp Asn Asn Gln Lys Asn Val Lys Ile Ser Asn
             75                  80                  85

GGA ATT GCG GAA CTA ACG ATG AGG CAT AAC GCC AAT AAT ACC CCA CCT       1180
Gly Ile Ala Glu Leu Thr Met Arg His Asn Ala Asn Asn Thr Pro Pro
             90                  95                 100

GAC GGA GGA ACC TAT TTC ACC TCT GGG ATA TTT AAG TCG TAC CAA AAA       1228
Asp Gly Gly Thr Tyr Phe Thr Ser Gly Ile Phe Lys Ser Tyr Gln Lys
            105                 110                 115

TTT ACG TAT GGA TAC TTT GAG GCC AAA ATC CAA GGA GCG GAT ATA GGT       1276
Phe Thr Tyr Gly Tyr Phe Glu Ala Lys Ile Gln Gly Ala Asp Ile Gly
            120                 125                 130

GAA GGC GTA TGC CCA TCG TTT TGG CTT TAT AGT GAT TTC GAC TAT TCC       1324
Glu Gly Val Cys Pro Ser Phe Trp Leu Tyr Ser Asp Phe Asp Tyr Ser
135                 140                 145                 150

GTA GCC AAT GGG GAA ACG GTA TAC AGT GAA ATA GAT GTA GTT GAA CTA       1372
Val Ala Asn Gly Glu Thr Val Tyr Ser Glu Ile Asp Val Val Glu Leu
                155                 160                 165

CAA CAA TTC GAT TGG TAT GAA GGC CAT CAG GAC GAC ATT TAC GAC ATG       1420
Gln Gln Phe Asp Trp Tyr Glu Gly His Gln Asp Asp Ile Tyr Asp Met
            170                 175                 180

GAC TTA AAT CTA CAC GCC GTT GTC AAA GAA AAC GGA CAG GGG GTT TGG       1468
Asp Leu Asn Leu His Ala Val Val Lys Glu Asn Gly Gln Gly Val Trp
            185                 190                 195

AAA AGG CCA AAA ATG TAC CCT CAA GAA CAG TTG AAC AAA TGG AGA GCC       1516
Lys Arg Pro Lys Met Tyr Pro Gln Glu Gln Leu Asn Lys Trp Arg Ala
            200                 205                 210

ATG GAC CCG AGT AAA GAC TTT CAT ATC TAT GGT TGT GAA GTG AAC CAG       1564
Met Asp Pro Ser Lys Asp Phe His Ile Tyr Gly Cys Glu Val Asn Gln
215                 220                 225                 230

AAC GAA ATC ATA TGG TAT GTT GAC GGT GTC GAG GTT GCC CGA AAA CCA       1612
Asn Glu Ile Ile Trp Tyr Val Asp Gly Val Glu Val Ala Arg Lys Pro
                235                 240                 245

AAT AAA TAT TGG CAT CGC CCC ATG AAC GTT ACC CTT TCA TTG GGA CTC       1660
Asn Lys Tyr Trp His Arg Pro Met Asn Val Thr Leu Ser Leu Gly Leu
            250                 255                 260

AGA AAA CCA TTT GTG AAA TTT TTC GAC AAT AAG AAC AAT GCC ATA AAT       1708
Arg Lys Pro Phe Val Lys Phe Phe Asp Asn Lys Asn Asn Ala Ile Asn
```

```
              265                 270                 275
CCA GAA ACC GAT GCC AAG GCA AGG GAA AAA TTA TCG GAT ATA CCT ACA      1756
Pro Glu Thr Asp Ala Lys Ala Arg Glu Lys Leu Ser Asp Ile Pro Thr
    280                 285                 290

TCG ATG TAT GTG GAT TAC GTT CGG GTC TGG GAA AAA TCA GCA GGT AAC      1804
Ser Met Tyr Val Asp Tyr Val Arg Val Trp Glu Lys Ser Ala Gly Asn
295                 300                 305                 310

ACT ACC AAT CCC CCA ACC AGC GAG GTC GGC ACA CTA AAA ACA AAG GGT      1852
Thr Thr Asn Pro Pro Thr Ser Glu Val Gly Thr Leu Lys Thr Lys Gly
                315                 320                 325

TCG AAA CTG GTG ATT GAC CAT TGG GAT GCA AGT ACA GGG ACT ATT TCG      1900
Ser Lys Leu Val Ile Asp His Trp Asp Ala Ser Thr Gly Thr Ile Ser
            330                 335                 340

GCT GTC AGT AAC AAT ACA AAG ACA GGT CAA TAT GCC GGT TCA GTG AAC      1948
Ala Val Ser Asn Asn Thr Lys Thr Gly Gln Tyr Ala Gly Ser Val Asn
        345                 350                 355

AAC GCG AGC ATC GCC CAG ATA GTA ACA TTA AAA GCG AAT ACT TCA TAT      1996
Asn Ala Ser Ile Ala Gln Ile Val Thr Leu Lys Ala Asn Thr Ser Tyr
    360                 365                 370

AAG GTA TCG GCT TTC GGA AAG GCC AGC TCA CCC GGA ACA TCG GCT TAT      2044
Lys Val Ser Ala Phe Gly Lys Ala Ser Ser Pro Gly Thr Ser Ala Tyr
375                 380                 385                 390

CTA GGC ATT AGT AAA GCA TCC AAC AAC GAA CTC ATA AGC AAT TTT GAA      2092
Leu Gly Ile Ser Lys Ala Ser Asn Asn Glu Leu Ile Ser Asn Phe Glu
                395                 400                 405

TTC AAA ACA ACC TCA TAC TCC AAA GGC GAG ATT GAG ATA AGA ACT GGA      2140
Phe Lys Thr Thr Ser Tyr Ser Lys Gly Glu Ile Glu Ile Arg Thr Gly
            410                 415                 420

AAT GTT CAG GAA TCA TAT CGC ATA TGG TAT TGG TCT TCC GGG CAA GCC      2188
Asn Val Gln Glu Ser Tyr Arg Ile Trp Tyr Trp Ser Ser Gly Gln Ala
        425                 430                 435

TAT TGC GAT GAT TTT AAC CTT GTT GAA ATA AAC AGC GGG GCT TCA CAA      2236
Tyr Cys Asp Asp Phe Asn Leu Val Glu Ile Asn Ser Gly Ala Ser Gln
    440                 445                 450

CTC AAT GAA AAT GAG ACT GAA ACA GCA CTG GAA AAA GGT ATA CAC ATT      2284
Leu Asn Glu Asn Glu Thr Glu Thr Ala Leu Glu Lys Gly Ile His Ile
455                 460                 465                 470

TAT CCG AAT CCC TAT AAA AAC GGT CCA TTG ACA TCG ATT TTT GGC AAA      2332
Tyr Pro Asn Pro Tyr Lys Asn Gly Pro Leu Thr Ile Asp Phe Gly Lys
                475                 480                 485

CCC TTC AGC GGC GAG GTC CAA ATC ACC GGT TTA AAC GGT AGA ACA TTC      2380
Pro Phe Ser Gly Glu Val Gln Ile Thr Gly Leu Asn Gly Arg Thr Phe
            490                 495                 500

TTA AGA AGA AAT GTT GTC GAT CAA ACT TCG GTT CAG CTC CTA GAA TCC      2428
Leu Arg Arg Asn Val Val Asp Gln Thr Ser Val Gln Leu Leu Glu Ser
        505                 510                 515

AAA TCT AAA TTC AAG AGC GGT CTA TAT ATC GTT AAA ATT AGT GGC CCG      2476
Lys Ser Lys Phe Lys Ser Gly Leu Tyr Ile Val Lys Ile Ser Gly Pro
    520                 525                 530

GAT GGA GAG GTT TCA AAA AAG ATA CTC GTG GAG TAACTAAAAA TCAATTTTTA   2529
Asp Gly Glu Val Ser Lys Lys Ile Leu Val Glu
535                 540                 545

CAGGATTACA GACGGGCAAA GGGATTTTCC TTTGCCCGTT TTTAAAATTA TGGGCGGAAA   2589

CGATTGTTGC G                                                        2600
```

(2) INFORMATION FOR SEQ ID NO: 8:

(i) SEQUENCE CHARACTERISTICS:
        (A) LENGTH: 545 amino acids (B) TYPE: amino acid
    (D) TOPOLOGY: linear (ii) MOLECULE TYPE: protein (xi) SEQUENCE DESCRIPTION: SEQ ID NO: 8:

```
Met Lys Lys Pro Asn Phe Tyr Gly Lys Met Gly Arg Thr Ala Leu Ser
 1               5                  10                  15

Ser Leu Phe Tyr Leu Phe Phe Leu Gly Leu Val Tyr Gly Gln Gln Pro
            20                  25                  30

Thr Lys Thr Ser Asn Pro Asn Asp Gln Trp Thr Ile Lys Trp Ser Ala
        35                  40                  45

Ser Asp Glu Phe Asn Lys Asn Asp Pro Asp Trp Ala Lys Trp Ile Lys
50                  55                  60

Thr Gly Asn Leu Pro Asn Thr Ser Ala Trp Lys Trp Asn Asn Gln Lys
65                  70                  75                  80

Asn Val Lys Ile Ser Asn Gly Ile Ala Glu Leu Thr Met Arg His Asn
                85                  90                  95

Ala Asn Asn Thr Pro Pro Asp Gly Gly Thr Tyr Phe Thr Ser Gly Ile
            100                 105                 110

Phe Lys Ser Tyr Gln Lys Phe Thr Tyr Gly Tyr Phe Glu Ala Lys Ile
        115                 120                 125

Gln Gly Ala Asp Ile Gly Glu Gly Val Cys Pro Ser Phe Trp Leu Tyr
130                 135                 140

Ser Asp Phe Asp Tyr Ser Val Ala Asn Gly Glu Thr Val Tyr Ser Glu
145                 150                 155                 160

Ile Asp Val Val Glu Leu Gln Gln Phe Asp Trp Tyr Glu Gly His Gln
                165                 170                 175

Asp Asp Ile Tyr Asp Met Asp Leu Asn Leu His Ala Val Val Lys Glu
            180                 185                 190

Asn Gly Gln Gly Val Trp Lys Arg Pro Lys Met Tyr Pro Gln Glu Gln
        195                 200                 205

Leu Asn Lys Trp Arg Ala Met Asp Pro Ser Lys Asp Phe His Ile Tyr
210                 215                 220

Gly Cys Glu Val Asn Gln Asn Glu Ile Ile Trp Tyr Val Asp Gly Val
225                 230                 235                 240

Glu Val Ala Arg Lys Pro Asn Lys Tyr Trp His Arg Pro Met Asn Val
                245                 250                 255

Thr Leu Ser Leu Gly Leu Arg Lys Pro Phe Val Lys Phe Phe Asp Asn
            260                 265                 270

Lys Asn Asn Ala Ile Asn Pro Glu Thr Asp Ala Lys Ala Arg Glu Lys
        275                 280                 285

Leu Ser Asp Ile Pro Thr Ser Met Tyr Val Asp Tyr Arg Val Trp
290                 295                 300

Glu Lys Ser Ala Gly Asn Thr Thr Asn Pro Pro Thr Ser Glu Val Gly
305                 310                 315                 320

Thr Leu Lys Thr Lys Gly Ser Lys Leu Val Ile Asp His Trp Asp Ala
                325                 330                 335

Ser Thr Gly Thr Ile Ser Ala Val Ser Asn Asn Thr Lys Thr Gly Gln
            340                 345                 350

Tyr Ala Gly Ser Val Asn Asn Ala Ser Ile Ala Gln Ile Val Thr Leu
        355                 360                 365

Lys Ala Asn Thr Ser Tyr Lys Val Ser Ala Phe Gly Lys Ala Ser Ser
370                 375                 380
```

```
                                -continued

Pro Gly Thr Ser Ala Tyr Leu Gly Ile Ser Lys Ala Ser Asn Asn Glu
385                 390                 395                 400

Leu Ile Ser Asn Phe Glu Phe Lys Thr Thr Ser Tyr Ser Lys Gly Glu
                405                 410                 415

Ile Glu Ile Arg Thr Gly Asn Val Gln Glu Ser Tyr Arg Ile Trp Tyr
            420                 425                 430

Trp Ser Ser Gly Gln Ala Tyr Cys Asp Asp Phe Asn Leu Val Glu Ile
        435                 440                 445

Asn Ser Gly Ala Ser Gln Leu Asn Glu Asn Glu Thr Glu Thr Ala Leu
    450                 455                 460

Glu Lys Gly Ile His Ile Tyr Pro Asn Pro Tyr Lys Asn Gly Pro Leu
465                 470                 475                 480

Thr Ile Asp Phe Gly Lys Pro Phe Ser Gly Glu Val Gln Ile Thr Gly
                485                 490                 495

Leu Asn Gly Arg Thr Phe Leu Arg Arg Asn Val Val Asp Gln Thr Ser
            500                 505                 510

Val Gln Leu Leu Glu Ser Lys Ser Lys Phe Lys Ser Gly Leu Tyr Ile
        515                 520                 525

Val Lys Ile Ser Gly Pro Asp Gly Glu Val Ser Lys Lys Ile Leu Val
    530                 535                 540

Glu
545
```